US010638966B2

(12) United States Patent
Elia et al.

(10) Patent No.: US 10,638,966 B2
(45) Date of Patent: May 5, 2020

(54) POINT OF CARE URINE ANALYZER

(71) Applicant: ART Healthcare Ltd., Natania (IL)

(72) Inventors: Liron Elia, Kiryat-Ata (IL); Gavriel J. Iddan, Haifa (IL)

(73) Assignee: ART Healthcare Ltd., Natania (IL)

( * ) Notice: Subject to any disclaimer, the term of this patent is extended or adjusted under 35 U.S.C. 154(b) by 0 days.

(21) Appl. No.: 15/228,115

(22) Filed: Aug. 4, 2016

(65) Prior Publication Data
US 2017/0035342 A1   Feb. 9, 2017

Related U.S. Application Data

(60) Provisional application No. 62/201,118, filed on Aug. 5, 2015.

(51) Int. Cl.
*A61B 5/20* (2006.01)
*A61M 25/00* (2006.01)
(Continued)

(52) U.S. Cl.
CPC ........... *A61B 5/208* (2013.01); *A61B 5/1455* (2013.01); *A61B 5/1468* (2013.01); *A61B 5/14507* (2013.01); *A61B 5/201* (2013.01); *A61B 5/746* (2013.01); *A61B 5/7475* (2013.01); *A61M 25/0017* (2013.01); *A61B 5/412* (2013.01);
(Continued)

(58) Field of Classification Search
None
See application file for complete search history.

(56) References Cited

U.S. PATENT DOCUMENTS 3,591,290 A * 7/1971 Zinner .................. A61B 5/208
356/335
3,664,339 A   5/1972 Santomieri
(Continued)

FOREIGN PATENT DOCUMENTS

EP    0112699        7/1984
JP    04-051963      2/1992
(Continued)

OTHER PUBLICATIONS

S.T. Thoroddsen, High-Speed Imaging of Drops and Bubbles, Annu. Rev. Fluid Mech. 2008. 40:257-85 | DOI: 10.1146/annurev.fluid.40.111406.102215.*
(Continued)

*Primary Examiner* — Sean P Dougherty
*Assistant Examiner* — Benjamin S Melhus

(57) ABSTRACT

There is provided a urine analysis device for bed side monitoring of a patient, comprising: an inlet sized and shaped for fluid communication with a urine collecting tube that receives urine from a patient; a drip chamber through which the urine flows towards an outlet; at least one sensor that analyzes each drop of urine and estimates a respective volume of each drop; a timing element that measures a reference time for each drop; a program store storing code; and at least one processing unit coupled to the program store for implementing the stored code, the code comprising: code to calculate a urine output flow rate of the urine output flowing through the chamber according to the estimated volume of each drop of the urine and the reference time for each drop; and code to output the urine output flow rate.

20 Claims, 17 Drawing Sheets

(51) Int. Cl.
  *A61B 5/00* (2006.01)
  *A61B 5/1455* (2006.01)
  *A61B 5/145* (2006.01)
  *A61B 5/1468* (2006.01)

(52) U.S. Cl.
  CPC ....... *A61B 5/743* (2013.01); *A61B 2562/0295* (2013.01)

(56) References Cited

U.S. PATENT DOCUMENTS

| | | | |
|---|---|---|---|
| 3,776,229 A | 12/1973 | McPhee | |
| 4,038,982 A | 8/1977 | Burke et al. | |
| 4,173,224 A * | 11/1979 | Marx | G05D 7/0623 128/DIG. 13 |
| 4,181,130 A * | 1/1980 | Bailey | A61M 5/1689 128/DIG. 13 |
| 4,261,388 A | 4/1981 | Shelton | |
| 4,314,484 A * | 2/1982 | Bowman | G01F 3/00 128/DIG. 13 |
| 4,432,761 A * | 2/1984 | Dawe | G01F 3/00 222/420 |
| 4,432,762 A * | 2/1984 | Dawe | A61M 5/1689 250/559.21 |
| 4,490,140 A * | 12/1984 | Carr | A61M 5/1689 128/DIG. 13 |
| 4,498,901 A * | 2/1985 | Finch | A61M 5/1689 128/DIG. 13 |
| 4,504,263 A | 3/1985 | Steuer et al. | |
| 4,525,163 A | 6/1985 | Slavik et al. | |
| 4,533,350 A | 8/1985 | Danby et al. | |
| 4,820,281 A | 4/1989 | Lawler, Jr. | |
| 4,936,828 A | 6/1990 | Chiang | |
| 5,186,057 A * | 2/1993 | Everhart | A61M 5/1689 250/575 |
| 5,377,101 A * | 12/1994 | Rollema | A61B 5/208 422/68.1 |
| 5,444,527 A * | 8/1995 | Kosaka | G01N 15/1459 356/317 |
| 5,621,392 A * | 4/1997 | Paolini | A61M 5/1689 128/DIG. 13 |
| 5,684,584 A * | 11/1997 | Nakamoto | G01N 15/14 356/336 |
| 5,747,671 A | 5/1998 | Hirota et al. | |
| 5,856,200 A | 1/1999 | Krause et al. | |
| 5,938,643 A * | 8/1999 | Lerner | A61M 5/1689 604/251 |
| 5,982,289 A | 11/1999 | Kingsley et al. | |
| 6,032,016 A | 2/2000 | Morigami et al. | |
| 6,235,242 B1 * | 5/2001 | Small | G01N 21/01 422/62 |
| 6,731,387 B2 * | 5/2004 | Neimark | G01N 15/082 356/435 |
| 2004/0171983 A1 | 9/2004 | Sparks et al. | |
| 2007/0238954 A1 | 10/2007 | White et al. | |
| 2008/0221551 A1 | 9/2008 | Goodson et al. | |
| 2009/0314101 A1 | 12/2009 | Levine | |
| 2010/0160789 A1 | 6/2010 | Dilworth et al. | |
| 2010/0309005 A1 | 12/2010 | Warner et al. | |
| 2011/0009817 A1 | 1/2011 | Bennett et al. | |
| 2011/0046516 A1 * | 2/2011 | Paz | A61B 5/14507 600/584 |
| 2011/0249255 A1 | 10/2011 | Bentien | |
| 2012/0095433 A1 | 4/2012 | Hungerford et al. | |
| 2012/0179387 A1 * | 7/2012 | Deng | G09B 23/303 702/19 |
| 2013/0083191 A1 * | 4/2013 | Lowery | G05D 7/0635 348/135 |
| 2013/0201471 A1 | 8/2013 | Bui et al. | |
| 2013/0201482 A1 | 8/2013 | Munro | |
| 2013/0310990 A1 | 11/2013 | Peret et al. | |
| 2014/0116128 A1 * | 5/2014 | Mantinband | G01F 1/6847 73/204.11 |
| 2014/0273265 A1 * | 9/2014 | Feingold | G01N 27/08 436/163 |
| 2014/0318639 A1 | 10/2014 | Peret et al. | |
| 2016/0146654 A1 | 5/2016 | Elia et al. | |

FOREIGN PATENT DOCUMENTS

| | | |
|---|---|---|
| JP | 07-333231 | 12/1995 |
| WO | WO 2009/142508 | 11/2009 |
| WO | WO 2014/052137 | 4/2014 |
| WO | WO 2016/084080 | 6/2016 |
| WO | WO 2017/021971 | 2/2017 |

OTHER PUBLICATIONS

Jesse B. Hoagg et al., Sliding Window Recursive Quadratic Optimization with Variable Regularization, Jul. 1, 2011, 2011 American Control Conference, pp. 1-6.*
Communication Relating to the Results of the Partial International Search dated Nov. 14, 2016 From the International Searching Authority Re. Application No. PCT/IL2016/050855. (10 Pages).
International Search Report and the Written Opinion dated Mar. 1, 2016 From the International Searching Authority Re. Application No. PCT/IL2015/051143.
Restriction Official Action dated Apr. 26, 2016 From the Re. U.S. Appl. No. 14/951,256.
Official Action dated Aug. 9, 2016 From the Re. U.S. Appl. No. 14/951,256.
AKI "Section2: AKI Definition: Chap.2.1: Definition and Classification of AKI", Kidney International Supplements, 2(Chap.2.1): 19-36, Feb. 29, 2012.
Labib et al. "Volume Management in the Crittically Ill Patient With Acute Kidney Injury", Critical Care Research and Practice, 2013(Art ID 792830): 1-8, Feb. 7, 2013.
Ralib et al. "The Urine Output Definition of Acute Kidney Injury Is Too Liberal", Critical Care, 17(3): R112-1-R112-11, Published Online Jun. 20, 2013.
Applicant-Initiated Interview Summary dated May 26, 2017 From the Re. U.S. Appl. No. 14/951,256. (9 pages).
Official Action dated Feb. 23, 2017 From the Re. U.S. Appl. No. 14/951,256. (39 pages).
International Search Report and the Written Opinion dated Jan. 12, 2017 From the International Searching Authority Re. Application No. PCT/IL2016/050855. (19 Pages).
Official Action dated Jul. 28, 2017 From the Re. U.S. Appl. No. 14/951,256. (25 pages).
International Preliminary Report on Patentability dated Feb. 15, 2018 From the International Bureau of WIPO Re. Application No. PCT/IL2016/050855. (13 Pages).
Official Action dated Feb. 5, 2018 From the Re. U.S. Appl. No. 14/951,256. (35 pages).
Supplementary European Search Report and the European Search Opinion dated Jul. 23, 2018 From the European Patent Office Re. Application No. 15863318.0. (10 Pages).

* cited by examiner

POINT OF CARE URINE ANALYZER

RELATED APPLICATION

This application claims the benefit of priority under 35 USC § 119(e) of U.S. Provisional Patent Application No. 62/201,118 filed Aug. 5, 2015, the contents of which are incorporated herein by reference in their entirety.

FIELD AND BACKGROUND OF THE INVENTION

The present invention, in some embodiments thereof, relates to urine analysis and, more specifically, but not exclusively, to systems and methods for point of care urine analysis.

Urine flow and/or measurement of urine constituents are used by the medical community as an indicator of health in general, and in particular in the case of hospitalized patients and/or post surgical patients. Current medical practice is based on measuring urine output of patients (e.g., using an indwelling catheter) by manual observation using grades marked on a urine collection bag. Decreased urine flow may be indicative of, for example, acute kidney injury (AKI). Increased urine flow may be indicative of, for example, post obstructive dieresis (POD). Urine analysis is performed by using a urine test strip that is manually dipped into the urine. Colors appearing on the test strip are visually compared to a reference. When more accurate values are required, a urine sample is sent to a lab for analysis.

SUMMARY OF THE INVENTION

According to an aspect of some embodiments of the present invention there is provided a urine analysis device for bed side monitoring of a patient, comprising: an inlet sized and shaped for fluid communication with a urine collecting tube that receives urine from a patient; a drip chamber through which the urine flows towards an outlet; at least one sensor that analyzes each drop of urine and estimates a respective volume of each drop; a timing element that measures a reference time for each drop; a program store storing code; and at least one processing unit coupled to the program store for implementing the stored code, the code comprising: code to calculate a urine output flow rate of the urine output flowing through the chamber according to the estimated volume of each drop of the urine and the reference time for each drop; and code to output the urine output flow rate.

Optionally, the urine analysis device further comprises code to identify a trend in the urine output flow rate indicative of a decrease or increase in the urine output flow rate and to present an indication of the trend on a graphical user interface (GUI) presented on a display.

Optionally, the urine analysis device further comprises code to identify a trend in the urine output flow rate indicative of acute kidney injury (AKI) and to present an indication of the detected AKI on the GUI.

Optionally, the urine analysis device further comprises code to generate an alert when an analysis of the trend is predictive of a future urine flow rate value falling outside of a predefine tolerance range.

Optionally, the trend is identified according to a least square regression analysis conducted using a sliding window of a predefined number of urine output flow rate measurements.

Optionally, the code includes instructions to calculate an instantaneous urine output flow rate, and present the instantaneous urine output flow rate on the GUI.

Optionally, the urine analysis device further comprises an interface to a display, and code that instructions a presentation of a graphical user interface (GUI) on the display that includes the measured urine output flow rate and an identified trend in the urine output flow rate.

Optionally, the sensors analyzes urine flowing within the drip chamber, prior to the flowing urine entering a urine collection bag in fluid communication with the outlet.

Optionally, the sensor comprises a fast gated camera that is activated by a photo detector disposed above the camera to capture at least one image of each drop, and further comprising code to estimate the volume of each drop according to an analysis of the at least one image of the drop.

Optionally, the fast gated camera includes a high resolution image sensor selected from a group consisting of: a complementary metal oxide semiconductor (CMOS) module, and a charge couple device (CCD) module.

Optionally, the code comprising code instructions to calculate a type of content of the drop by combining a plurality of time sequentially ordered calculated values of widths of the drop and a plurality of time sequentially ordered values of widths of a plurality of exemplary drops, the plurality of exemplary drops comprising of different content types of liquid, wherein a respective drop is calculated to be of a one of a plurality of the types of liquid.

Optionally, the drip chamber is transparent, and wherein the sensor comprises an optical sensor for estimating the volume of the urine drop through the walls of the transparent drip chamber.

Optionally, the urine analysis device further comprises a drip formation element that forms the urine outputted by the patient into the drops of urine that one drop at a time inside the drip chamber.

According to an aspect of some embodiments of the present invention there is provided a urine analysis device for bed side monitoring of a patient, comprising: an inlet sized and shaped for fluid communication with a urine collecting tube that receives urine from a patient; a drip chamber through which the urine flows towards an outlet; a plurality of constituent measuring elements positioned within the drip chamber below the inlet to contact drops of urine received from the patient, the constituent measuring elements arranged on a rotating element that turns a predefined amount at a predefined time interval to expose another of the constituent measuring elements to a new drop of urine, wherein each of the constituent measuring elements estimates a concentration of a different urine constituent in respective drops of urine; and at least one sensor coupled to the constituent measuring elements to output a constituent signal indicative of a measurement of the respective urine constituent by the respective measuring element.

Optionally, the urine analysis device further comprises a program store storing code; and at least one processing unit coupled to the program store for implementing the stored code, the code comprising: code to analyze the constituent signal for each respective urine constituent to calculate at least one of a concentration and the presence of the respective urine constituent; and code to output the at least one of concentration and presence of each respective urine constituent.

Optionally, the constituent measuring elements and the at least one sensor comprise respective lab-on-chips each designed to estimate at least one of a concentration and a presence of a respective urine constituent.

Optionally, each of the constituent measuring elements includes an impregnated strip media that changes to a different color according to the concentration of the respective constituent, and wherein the at least one sensor comprises a color camera arranged to sense the changed color of each respective constituent measuring element on the rotating element at each turn and output and outputs a signal indicative of the sensed changed color, and code instructions that analyze the signal to calculate the concentration of the respective constituent corresponding to the sensed changed color.

Optionally, the constituent signal is generated based on an analysis conducted in urine flowing within the drip chamber, prior to the flowing urine entering a urine collection bag in fluid communication with the outlet.

Optionally, the urine analysis device further comprises a sensor that detect the drops and outputs a signal to trigger the rotation of the rotating element.

According to an aspect of some embodiments of the present invention there is provided a urine analysis device for bed side monitoring of a patient, comprising: an inlet sized and shaped for fluid communication with a urine collecting tube that receives urine from a patient; a drip chamber through which the urine flows towards an outlet; a light source that creates a light directed to pass through at least one drop of the urine of the patient; a dispersion element receives the light that passed through the at least drop of the urine and outputs a light spectrum; a multi element detector that receives the light spectrum on a plurality of light detector elements and output a signal indicative of the intensity of the received light spectrum as a function of the wavelength of light according to the respective light detector elements; a program store storing code; and at least one processing unit coupled to the program store for implementing the stored code, the code comprising: code to analyze the signal and calculate a value of at least one urine constituent; and code to output the value of the at least one urine constituent.

Optionally, the light source is a tunable light source capable of emitting a range of wavelengths.

Optionally, the light source is a sweeping source, wherein the spectral dispersion element splits the light source to a first portion that is reflected at least by the urine and directed to a sub-set of elements of the multi element detector and a second portion that passes through the urine and directed to another detector having a single detector, wherein the light source is swept as a function of time, and code instructions to calculate an osmolarity of the urine according to an analysis of the signals outputted by the multi element detector and the another detector.

Optionally, the urine analysis device further comprises an interferometer that includes a tunable source of the light source capable of emitting a range of wavelengths, a beam splitter that splits the light emitted by the light source to a reference path and a path through the urine, and a mechanism to combine the reference path light and the light of the path through the urine into a combined spectral signal, and further comprising code instructions to analyze the combined spectral signal to calculate concentration of at least one urine constituent.

Optionally, the urine analysis device further comprises a transparent chamber positioned within the drip chamber and arranged to be constantly maintained in a urine filled state, wherein the light of the path through the urine is directed through the transparent chamber.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
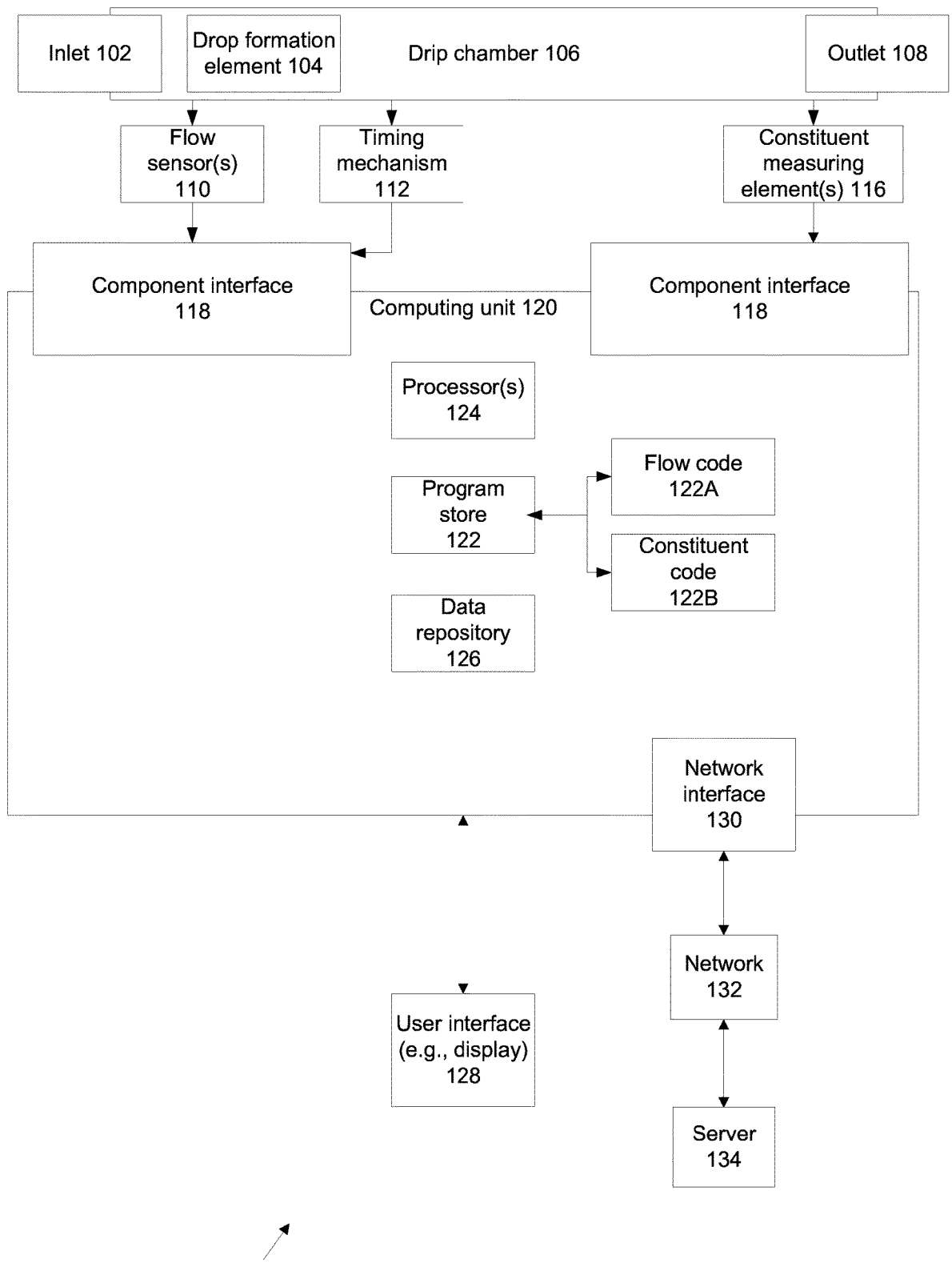
FIG. 1 is a block diagram of components of a system that uses formed urine drops to estimate a flow rate of urine outputted by a patient (using the volume measured for each drop), and/or estimates concentration of one or more constituents in the outputted urine, in accordance with some embodiments of the present invention.

The present invention, in some embodiments thereof, relates to urine analysis and, more specifically, but not exclusively, to systems and methods for point of care urine analysis.

An aspect of some embodiments of the present invention relates to a urine analysis device (and/or a method for operation of the urine analysis device implemented by code instructions executed by one or more processors) that calculates a urine outflow rate of urine outputted by a patient according to an estimated volume of one or more drops of urine and a time stamp indicative of formation of each respective drop being analyzed. The urine outputted by the patient (e.g., received from an indwelling urinary catheter) is formed into single dropped by a dripper element, for example, a hollow tube. A sensor analyzes one or more drops of urine and estimates the volume of each respective drop. A timing element determines the time for each respective drop, optionally as a time stamp. Code instructions executable by one or more processors calculate the urine outflow rate according to the volume and time stamp of the drops.

The urine analysis device provides bedside monitoring of the real-time urine output of the patient, for example, in comparison to standard manual methods in which urine accumulates for hours in a collection bag, and the accumulated volume is read visually using markings on the bag. Such methods require collection of urine for many hours before it can be determined whether the urine output is normal or abnormal, and therefore such methods are prone to error due to inaccuracies in volume and/or time estimations. The real-time data provided by the urine analysis device may be used by health care providers to provide treatment to the patient sooner using accurate values and/or based on predicted values, and/or prevent the patient from deteriorating and/or disease progression with earlier treatment provided by the real-time data and/or predicted data.

Optionally, a trend is identified (e.g., by code instructions executable by one or more processors) in the urine output flow rate. The identified trend is predictive of an increase or a decrease in the value of the urine output flow rate relative to a predefined tolerance range that represents a safe range of urine output flow rates for the patient.

Optionally the trend is indicative of acute kidney injury (AKI). The trend may be represented on a graphical user interface (GUI) that presents the calculated urine flow rate values, for example, as an arrow based on a regression line of the urine flow rate data points. An alert is optionally generated (e.g., flashing warning message on the GUI) when the trend is indicative that the urine output flow rate is predicted to reach a value outside of the predefined tolerance range in the near future (e.g., in the next hour, 6 hours, or 12 hours, or other future times).

Optionally, an instantaneous urine output flow rate is estimated (e.g., by code instructions executable by one or more processors) based on at least two urine drops. The instantaneous urine output flow rate may be presented on the GUI, and/or plotted as a point on a graph of urine flow rate as a function of time, which may be used to identify the trend.

The instantaneous urine output flow rate may be a more accurate and/or real-time representation of the state of the patient, for example, in comparison to standard manual methods in which the average urine flow rate is estimated using accumulated urine over many hours. Alternatively or additionally, the urine output flow rate is measured over a time interval that may be shorter than a time interval used by manual methods, for example, a half hour, or an hour. The urine output flow rate is measured using a sample or most or all of the urine drops that are outputted by the patient during the time interval. The urine output flow rate may provide a more accurate representation of the state of the patient, rather than having to wait for several hours for sufficient urine to accumulate for a manual reading.

The urine analysis device (and/or code instructions executed by one or more processors that perform the urine analysis) described herein provides automatic monitoring (e.g., continuous, periodic, and/or event based) of patients that is used to detect early changes in the patient's state of health, for example, early onset of AKI, urinary retention, urinary tract infection, and early onset of POD. The predictive trend may predict early progression to abnormal health states, for example, progression to AKI.

An aspect of some embodiments of the present invention relates to a urine analysis device (and/or a method for operation of the urine analysis device implemented by code instructions executed by one or more processors) that measures real-time values of one or more urinary constituents in urine outputted by the patient. Exemplary values include: the concentration measured for each individual constituent, the presence of each individual constituent using a threshold (e.g., zero, or other value), urine osmolarity, and urine osmolality.

The urine analysis device performs measurements of a different urine constituent for each sequentially received drop(s) of urine. Optionally, each sequential single drop or group of drops is used for measuring a different single constituent in the drop. For example, in contrast to standard manual methods, in which a urine dipstick is inserted into a large volume of urine for measurement of multiple constituents using the same urine volume. Alternatively or additionally, the single drop may be used to measure osmolality and/or osmolarity.

Optionally, each sequentially formed drop(s) falls onto a measuring element designed to measure a different constituent. Exemplary measuring elements include multiple lab-on-chip (LOC) units each designed to measure a different constituent, and media each designed to change to a different color according to a concentration of the respective constituent being measured by the respective media. A color camera may sense the color of each media and generate a signal indicative of the color. The signal may be analyzed using instruction code to estimate the concentration of the constituents. Alternatively or additionally, the LOC and/or other measuring elements may be used to measure osmolarity and/or osmolality.

Optionally, the measuring elements are arranged along a surface of a rotating element. The rotating element is controlled (e.g., by a motor) to turn a predefined amount to expose one or more sequentially formed drops to the measuring elements (each measuring element may receive one or more drops, for example, the minimum volume required to obtain an accurate reading).

For example, the rotating element turns at a predefined rate of rotation or indexing (e.g., manually set by the operator, according to manufacturer defined settings, based on formation of the drops and/or trigged by each falling drop), such that each drop (or multiple sequential drops) falls on a different measuring element that measures a different constituent of the drop. Alternatively, the rotation is triggered by a sensor detecting the falling drop to rotate the rotating element to expose the next measuring element to the falling drop.

An aspect of some embodiments of the present invention relates to systems and/or methods (e.g., code instructions executed by processor(s)) that estimates according to a spectral analysis, values of one or more urinary constituents in urine outputted by the patient. Measurements of the urinary constituents may be performed at predefined time intervals, for example, every 15 minutes, or every 60 minutes, or other time interval.

Exemplary values include: the concentration measured for each individual constituent, the presence of each individual constituent using a threshold (e.g., zero, or other value), urine osmolarity, and urine osmolality. A source of light (e.g., broadband light) is directed through the drop(s) of urine and optionally dispersed. Alternatively, the source of light is tunable, with narrow (e.g., single) bands of wavelengths of light directed (e.g., sequentially) through the drop(s). The light that passed the drop(s) of urine is directed towards a single or multi element detector array. Analysis code executed by one or more processors may analyze the intensity generated by the elements of the array, and/or according to which elements are activated, estimates the concentration of one or more urinary constituents, for example, by comparison with a standard reference (e.g., empirical measurements and/or calculated using a mathematical model).

Optionally, a TIR prism (or other light splitting implementation) splits the light generated by the light source to a first portion that is at least reflected by the urine and reaches a sub-set of the elements of the array. The light is split to a second portion that is transmitted through the urine and reaches a single element detector. The wavelength of the light is varied over time. The signals of the detector array and the single element detector are analyzed together to estimate the concentration of one or more urine constituents and/or the osmolarity and/or osmolality of the urine.

Alternatively or additionally, the light from the light source is split by a beam splitter into a reference beam, and a beam that passes through one or more drops of urine. The reference beam is combined with the light after passing through the urine, and analyzed to estimate the concentration of one or more urine constituents and/or the osmolarity and/or osmolality of the urine. For example, the signals may be subtracted from one another to arrive at a signal indicative of the urinary constituents (i.e., removing the reference light from the light that passed through the urine).

The systems (including the urine analysis devices) and/or methods described herein (e.g., code instructions executed by one or more processor(s)) address the technical problem of determining a urine flow and/or concentration of urinary constituent(s) that more accurately reflect the actual state of the patient. For example, current methods rely on an average manual measurement obtained over many hours, for example, manually reading a volume of urine collected in a bag over many hours, and dividing by the estimated number of hours, and/or manually dipping a urine stick into the volume of urine collected over many hours. The proposed solution provides an on-site (i.e., at the patient bedside) estimation of the urine flow rate and/or concentration of urinary constituents which more accurately relates to the real-time state of the patient, rather than a retrospective average view that the manual methods provide. The estimation may be used to predict beforehand that the patient urine flow rate and/or concentration of urinary constituents are trending towards leaving a safe predefined range.

The systems (including the urine analysis devices) and/or methods described herein (e.g., code instructions executed by one or more processor(s)) improve an underlying technical process within the technical field of urinalysis. The systems and/or methods described herein improve the process of estimating the patient urine flow rate (i.e., urinary output) and/or concentration of urine constituents, by providing real-time measurements at the bedside using formed drops of urine.

The systems (including the urine analysis devices) and/or methods described herein (e.g., code instructions executed by one or more processor(s)) improve performance of a computing unit executing the code instructions that estimate the patient urinary flow rate and/or estimate the concentration of urinary constituent(s). The improvement in performance is obtained by reducing the processing time, processing resources, and/or memory resources to compute the patient urinary flow rate and/or estimate the concentration of urinary constituent(s). The improvement in performance is achieved at least in part by the analysis over a predefined time interval using small volumes of urine (based on collecting one or several drops of urine), to calculate measurements, rather than, for example, collecting a large sample of urine over many hours to perform the measurement(s).

The systems (including the urine analysis devices) and/or methods described herein (e.g., code instructions executed by one or more processor(s)) are tied to physical real-life components, for example, using urine outputted by a patient (e.g., received from an indwelling urinary catheter), using electrical readings obtained from physical sensor(s), and/or presenting the measurements on a physical display.

The systems (including the urine analysis devices) and/or methods described herein (e.g., code instructions executed by one or more processor(s)) provide a unique, particular, and advanced technique of real-time or point-of-care (POC) estimation of the patient urine output flow rate and/or concentration of constituents in the outputted urine.

Accordingly, the systems and/or methods described herein are inextricably tied to computer technology and physical hardware, to overcome an actual technical problem arising in calculating more accurate values for patient urinary output and/or urinary constituents.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s).

In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms estimate, measure, and calculate are sometimes interchangeable, for example, when referring obtaining the urine output flow rate and/or urine constituent concentrations. For example, the sensor(s) may perform measurements on the drops of urine. The measurements are used for calculating the urine output flow rate and/or the urine constituent concentration. The calculated values represent an estimate of the actual values within the urine (i.e., based on extrapolation of the calculations performed on a sample of the urine).

Figure 2:
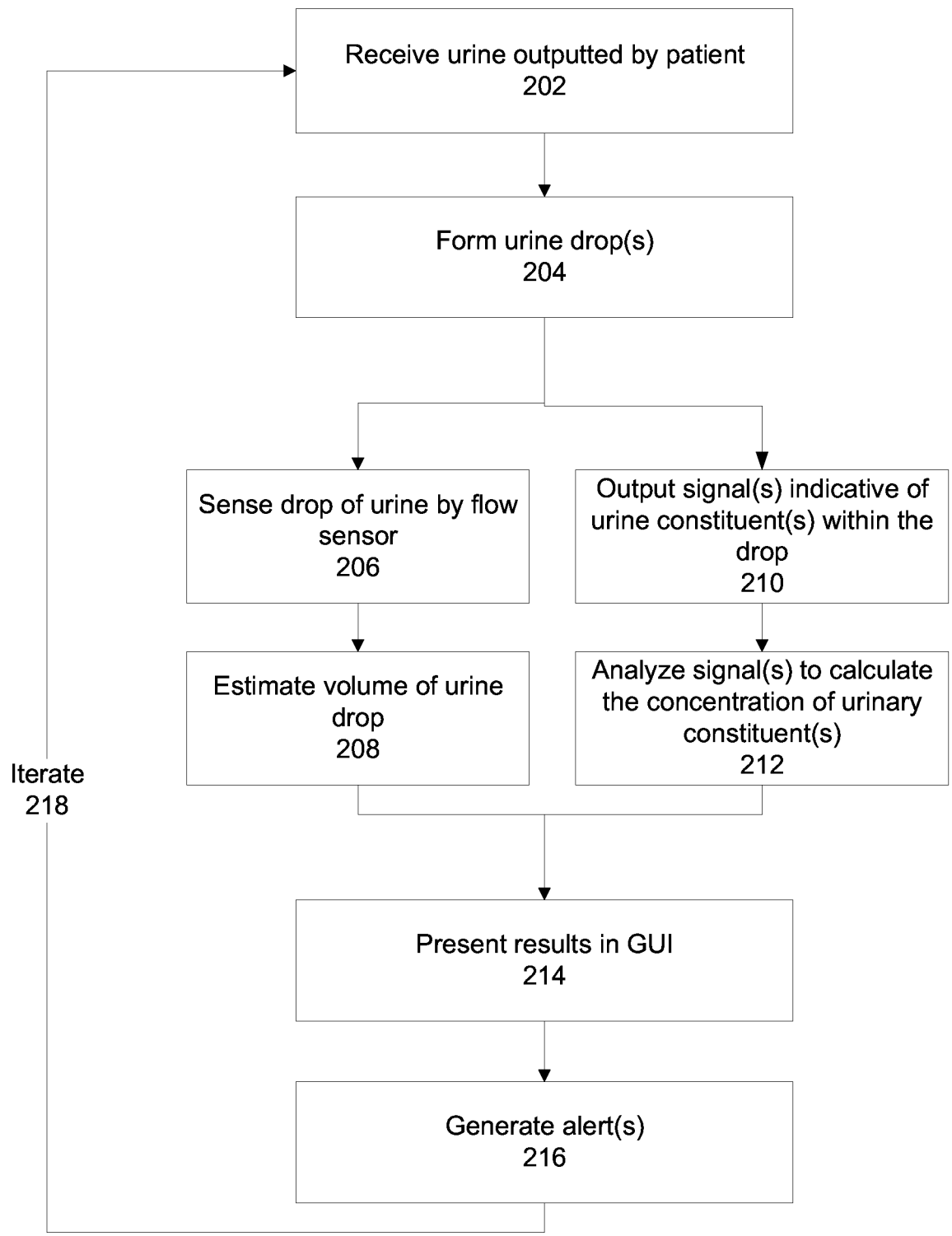
FIG. 2 is a flowchart of a method of operation of the system of FIG. 1, in accordance with some embodiments of the present invention.

Reference is now made to FIG. 1, which is a block diagram of components of a system 100 that uses formed urine drops to estimate a flow rate of urine outputted by a patient (using the volume measured for each drop), and/or estimates concentration of one or more constituents in the outputted urine, in accordance with some embodiments of the present invention. Reference is also made to FIG. 2, which is a flowchart of a method of operation of system 100 of FIG. 1, in accordance with some embodiments of the present invention.

System 100 includes an inlet 102 for fluid communication with a urine collecting tube that receives urine from the patient, for example, a connection to an output of an indwelling catheter positioned within the bladder of the patient. The urine received from inlet 102 is formed into single sequentially falling drops by a drip formation element 104 (e.g., hollow tube) that directs the drops into a drip chamber 106 having an outlet 108 to a urine collection system (e.g., bag, waste drainage). Dripper element 104 may be implemented, for example, as an elongated hollow tube that forms the drops at the end of the tube facing the group.

A flow sensor 110 (e.g., optical camera) analyzes each drop to estimate the volume of the drop, which is used to estimate the urine output flow rate, as described herein. Flow sensor 110 may be implemented as an electromagnetic sensor, optionally an optical sensor, optionally an optical camera that captures one or more images of the drop, optionally as the drop is falling through drip chamber 106.

Optionally, flow sensor 110 is a drop and/or drip measurement and/or analyzer, for example, as described in International Patent Application No. WO2016084080, filed on Nov. 24, 2015, by the same inventors as the present application, incorporated herein by reference in its entirety.

A timing mechanism 112 (e.g., clock connected to the optical camera) measures a time reference for each drop. The time reference may be an absolute time reference (e.g., the actual current time) and/or a relative time reference (e.g., the time elapsed from the previous drop, optionally resetting to zero for each new drop). The relative time is used to estimate the urine output flow rate, as described herein. Alternatively or additionally, timing mechanism 112 includes a counter that counts the number of drops that fall within a predefined time, for example, the number of drops per second, per minute, per hour, or other periods of time.

Constituent measuring element(s) 116 measure urinary constituents. Optionally, constituent measuring element 116 is implemented as a device that measures urine osmolarity and/or osmolality, for example, using spectral analysis, and/or implemented as an interferometer, as described herein. Alternatively or additionally, constituent measuring element(s) 116 are implemented as multiple elements each designed to measure the concentration (or presence of) a different urine constituent, for example, lab-on-chip, color strips or other bio-chemical sensor (as described herein).

Exemplary implementation of components 110, 112, and 116 are described herein.

It is noted that system 100 may be implemented using different combinations of components to perform desired measurements: flow sensor 110 and timing mechanism 112 (to measure the urine out flow rate), and/or constituent measuring element(s) 116 (to measure one or more constituents).

A component interface 118, which may include one or more physical and/or virtual interfaces provides connectivity between one or more components 110, 112, 116 and a computing unit 120. Component interface 118 may be implemented, for example, using one or more of: cable interface, wireless channel interface, application programming interface (API), software development kit (SDK) interface, and the like.

Computing unit 120 includes a program store 122 storing code instructions for implementation (i.e., instruction execution) by processor(s) 124, and/or a data repository 126. Program store 122 (and/or data repository 126) may store flow code 122A to calculate the urine output flow rate, constituent code 122B to calculate the concentration of one or more urinary constituents, and/or other code, for example, instructions to render the GUI that displays the trend and/or the calculated values (as described herein).

Processor(s) 124 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 124 may include one or more processors (homogenous or heterogeneous), which may be arranged for parallel processing, as clusters and/or as one or more multi core processing units.

Program store 122 stores code instructions implementable by processor(s) 124, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Data repository 126 may be implemented as, for example, a memory, a local hard-drive, a removable storage unit, an optical disk, a storage device, and/or as a remote server and/or computing cloud (e.g., accessed using a network connection).

Computing unit 120 may be in communication (e.g., using a suitable interface) with one or more user interfaces 128, optionally including a display, for example, a touch screen, a mouse, a keyboard, and/or a microphone with voice recognition software.

Computing unit 120 may include a network interface 130 (e.g., network interface card, wireless network connection, cable connection, virtual network interfaces, and the like) for connecting with one or more servers 132 over a network 134, for example, for transmitting the measurements to a remote monitoring server (e.g., located at a nurse's station) over a local wireless network, for transmitting the measurements to a storage server at a family physician's office over the internet.

Computing unit 120 may be implemented, for example, as a stand-alone portable unit (designed to be transferred between patient beds), a hardware card (or chip) implemented within an existing computer (e.g., desktop computer located on the ward), and/or a computer program product loaded within the existing computer (e.g., physician's laptop), and/or as an application on a mobile device (e.g., Smartphone, tablet, wearable computer such as computer glasses).

Figure 3:
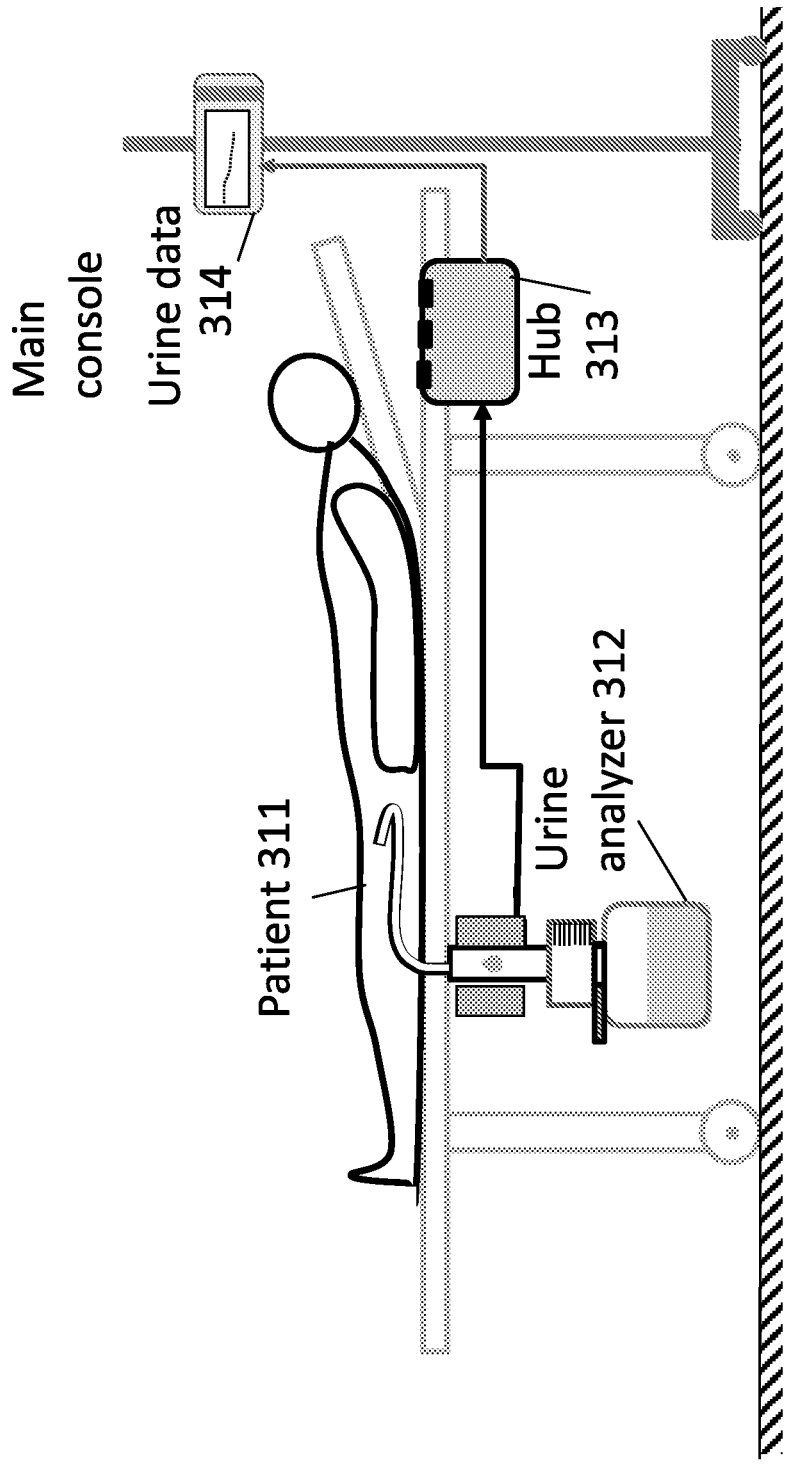
FIG. 3 is a schematic of an environment in which the system of FIG. 1 is implemented, in accordance with some embodiments of the present invention.

Reference is now made to FIG. 3, which is a schematic of an environment in which system 100 is implemented, in accordance with some embodiments of the present invention. Urine outputted by a patient 311 is received by a urine analyzer 312. The patient may be a hospitalized patient, a patient in a nursing home, or a patient being treated at home. The urine outputted by the patient may be collected by a catheter, optionally an indwelling urinary catheter (e.g., Foley catheter) that drains out the urine from the bladder as the urine is produced by the kidneys.

The urine is received and analyzed (as described herein) by urine analyzer 312, which may include one or more of the following components described with reference to FIG. 1: inlet 102, dripper element 104, drip chamber 106, outlet 108, flow sensor 110, timing mechanism 112, and constituent measuring element(s) 116. Urine analyzer 312 may be implemented as standalone portable device that may be positioned by the patient's bed. Urine analyzer 312 may be entirely disposable, or include one or more disposable components.

Signals generated by flow sensor 110, timing mechanism 112, and/or constituent measuring element(s) 116 are received and processed by a hub 313. Hub 313 may be an external unit in electrical communication with urine analyzer 312 (e.g., by a cable and/or wireless channel, and/or network), and/or hub 313 and urine analyzer 312 may be integrated into a single unit. Hub 313 may correspond to computing unit 120 described with reference to FIG. 1.

A main console 314 may be implemented as a display, optionally a touchscreen, and/or including a user input interface (e.g., buttons, keys), to display the calculated urine output flow rate and/or constituent concentration (i.e., urine data). Main console 314 may correspond to user interface 128 described with reference to FIG. 1.

Referring now back to FIG. 2, at 202, urine outputted by the patient is received by system 100.

System 100 operates under the assumption that urine received by inlet 102 is an accurate reflection of real-time urine production by the kidneys, within a tolerance requirement (e.g., range) representing remaining urine and/or variation in urine output due to urine within the bladder, leaks, and urine remaining within the catheter.

Inlet 102 may be implemented as a plastic tube, optionally flexible, optionally disposable that is sized to fit to the catheter. Inlet 102 may be integrated with the catheter.

At 204, the received urine is formed into drops by drop formation element 104, for example, a thin hollow tube sized and shaped to form individual drops at the opposite end of the end receiving the urine. Drop formation element 104 is sized and/or shaped and/or otherwise designed to not act as a bottleneck in the flow of urine. The rate at which drop formation element 104 is able to form the drops is designed to match the rate of urine outputted by the patient, such that drop formation element 104 does not act as a bottleneck in the flow of urine and inaccurately affect the estimation of the urinary flow rate.

The formed drops drip down into drip chamber 106, one drop at a time. The rate of the formation and dripping of the drops may be related to the urine output flow rate. Urine drops formed by the kidneys of the patient flow through the catheter for real-time analysis. Urine formed by the patient may not necessarily accumulate, other than, for example, the urine stored within the catheter and some residual urine within the bladder.

At 206, each drop is sensed, optionally imaged by flow sensor 110 and/or timed by timing mechanism 112. Inventors discovered that the volume of the drops of urine varies according to the make-up of the urine, for example, as shown by measured drop volume data for different liquids in FIG. 20 of International Patent Application No. WO2016084080. Since the volume of each drop varies according to the urine of the patient, which can vary dynamically for the same patient, the volume of a drop of urine cannot be accurately estimated. Measuring the volume of each drop of urine provide an accurate calculation of the urine output flow rate.

The volume of each drop is estimated by flow sensor(s) 110. Timing mechanism 112 measures the time of each drop (e.g., the elapsed time between drops, and/or the absolute time of each drop according to the actual time). The urine output flow rate is calculated according to the time and the volume measurements.

Flow sensor(s) 110 analyzes the drops of urine within drip chamber 106, prior to the flowing urine entering a urine collection bag in fluid communication with the outlet, for example, in comparison to other methods that determine the volume of fluid from the urine collected within the urine collection bag.

Figure 4:
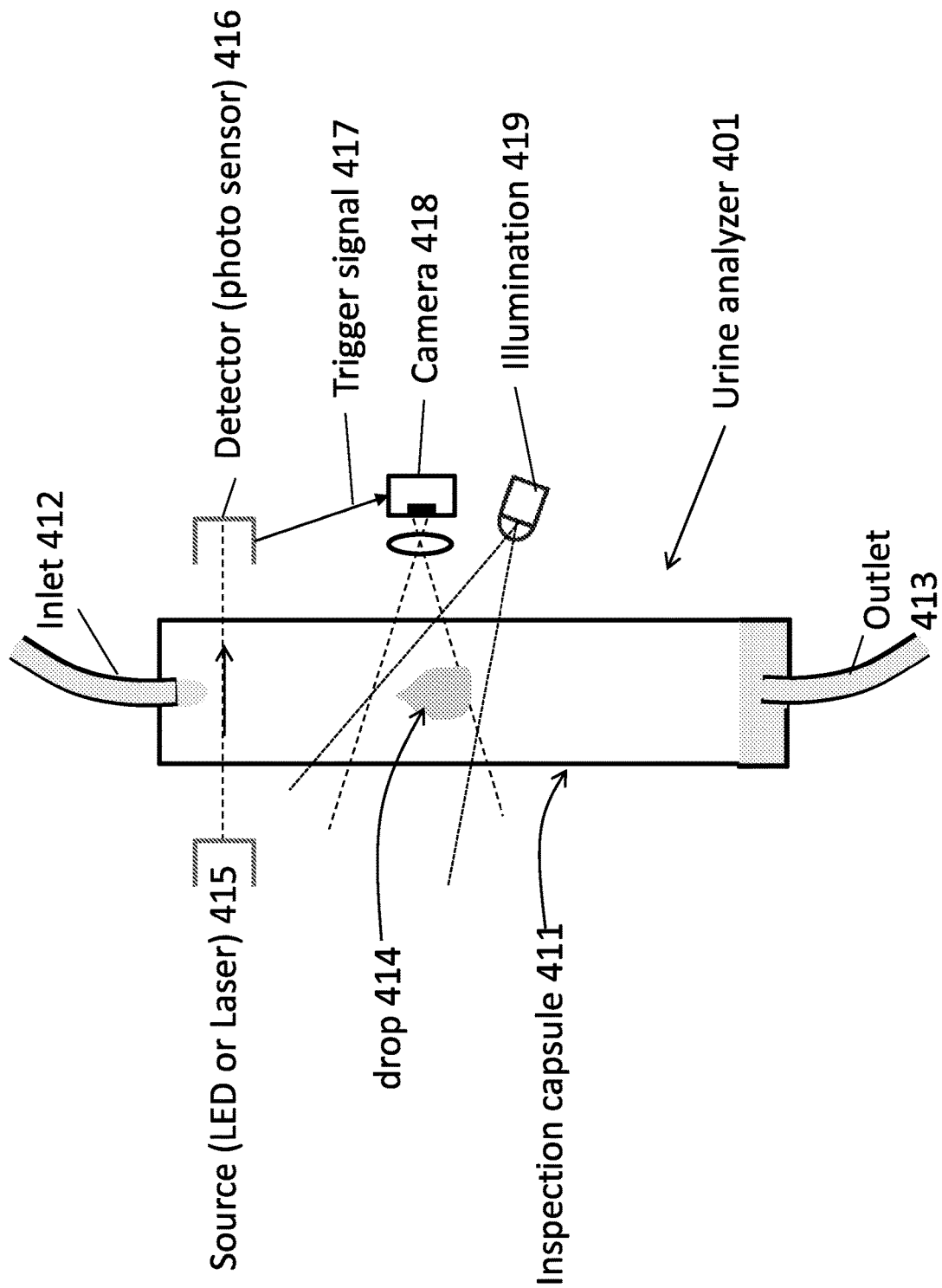
FIG. 4 is a schematic of an exemplary urine analyzer that outputs signals used to estimate the volume of a drop of urine and/or estimate the urine output flow rate, in accordance with some embodiments of the present invention.

Reference is now made to FIG. 4, which is a schematic of an exemplary urine analyzer 401 that outputs signals used to estimate the volume of a drop of urine and/or estimate the urine output flow rate (i.e., signals of the time of the drop), in accordance with some embodiments of the present invention.

Urine outputted by the patient is received by an inlet 412, which may correspond to inlet 102 described with reference to FIG. 1, and/or may connect to inlet 102, and/or may be an output of dripper element 104. Inlet 412 releases individual drops 414 of urine into a transparent (or translucent) inspection capsule 411 (which may correspond to drip chamber 106 described with reference to FIG. 1, and/or may be located within and/or in communication within drip chamber 106).

Each drop falling from inlet 412 triggers a detector 416, which may be implemented for example, as a photo sensor. Detector 416 may sense electromagnetic radiation (e.g., visible light, infrared light, laser) emitted by a source 415, for example, a laser, a light bulb, and/or a light emitting diode (LED). Source 415 and detector 416 may be positioned opposite each other, such that light from source 415 passes across the lumen of capsule 411 to reach detector 416. Falling drop 414 affects (e.g., disrupts, interrupts, and/or scatters) the electromagnetic transmission from source 415 to detector 416, generating a trigger signal 417.

Optionally, trigger signal 417 is used to determine the time of the triggering drop (e.g., relative elapsed time between drops, and/or absolute time of the drop) by timing mechanism 112 (e.g., circuitry, code instructions executed by one or more processors). Timing mechanism may be implemented including source 415 and detector 416.

A fast gated camera 418 is activated by trigger signal 417 outputted by photo detector 416 located above camera 418. Fast gated camera 418 may a high resolution image sensor, for example, a complementary metal oxide semiconductor (CMOS) module, and/or a charge couple device (CCD) module.

Camera 418 captures one or more images of each drop. An illumination element 419 (e.g., light) illuminates drop 414. The illumination may improve the quality of the image, by improving the accuracy of the estimation of the volume of the drop. Code instructions (e.g., flow code 122A) estimate the volume of each drop according to an analysis of the image of the drop, as described herein. Illumination element 419 may be positioned on the same side of capsule 411 as camera 418, or on the opposite side of camera 418. Illumination element 419 may be integrated with camera 418.

Optionally, the volume of the drop and/or the concentration of the urinary constitutes in the drop is calculated by calculating a type of content of the drop by combining multiple time sequentially ordered calculated values of widths of the drop, and time sequentially ordered values of widths of exemplary drops. The exemplary drops (e.g., stored in a template or library in data repository 126, based on empirically collected data and/or data calculated using a mathematical model) include different content types of liquid. The respective drop is calculated to be a one of the types of liquid, which allows for estimation of the volume and/or estimation of the concentration (e.g., osmolarity and/or osmolality). Additional details are provided, for example, with reference to WO2016084080.

Alternatively or additionally, the volume of the drop is estimated by constructing a 3D volume from the 2D images of the drop (e.g., using two cameras positioned at an angle relative to each other, optionally orthogonally positioned), and calculating the volume of the constructed drop. For example, the 2D image of the drop may be assumed to be symmetrical and rotated around a central longitudinal axis in the up-down direction to create the 3D volume of the drop.

Alternatively or additionally, as described with detail with reference to WO2016084080, the volume of the drop is calculated by summing volumes of horizontal planar segments of the drop. The volume of each horizontal planar segment of a drop is calculated by measuring the electromagnetic radiation (EMR) captured in a restricted horizontal planar area during a sequence of time intervals. As the drop falls, in each time interval a different horizontal segment of the drop interferes with a portion of EMR in the restricted horizontal planar area. The width of the horizontal segment of the drop is proportional to the amount of EMR that is interfered. The volume of the horizontal segment may be calculated when the width of the segment and the velocity of the segment are known.

After being analyzed, drops falling to the bottom of urine analyzer 401 may exit at outlet 413 (which may correspond to outlet 108 described with reference to FIG. 1, and/or may connect to outlet 108).

Figure 5:
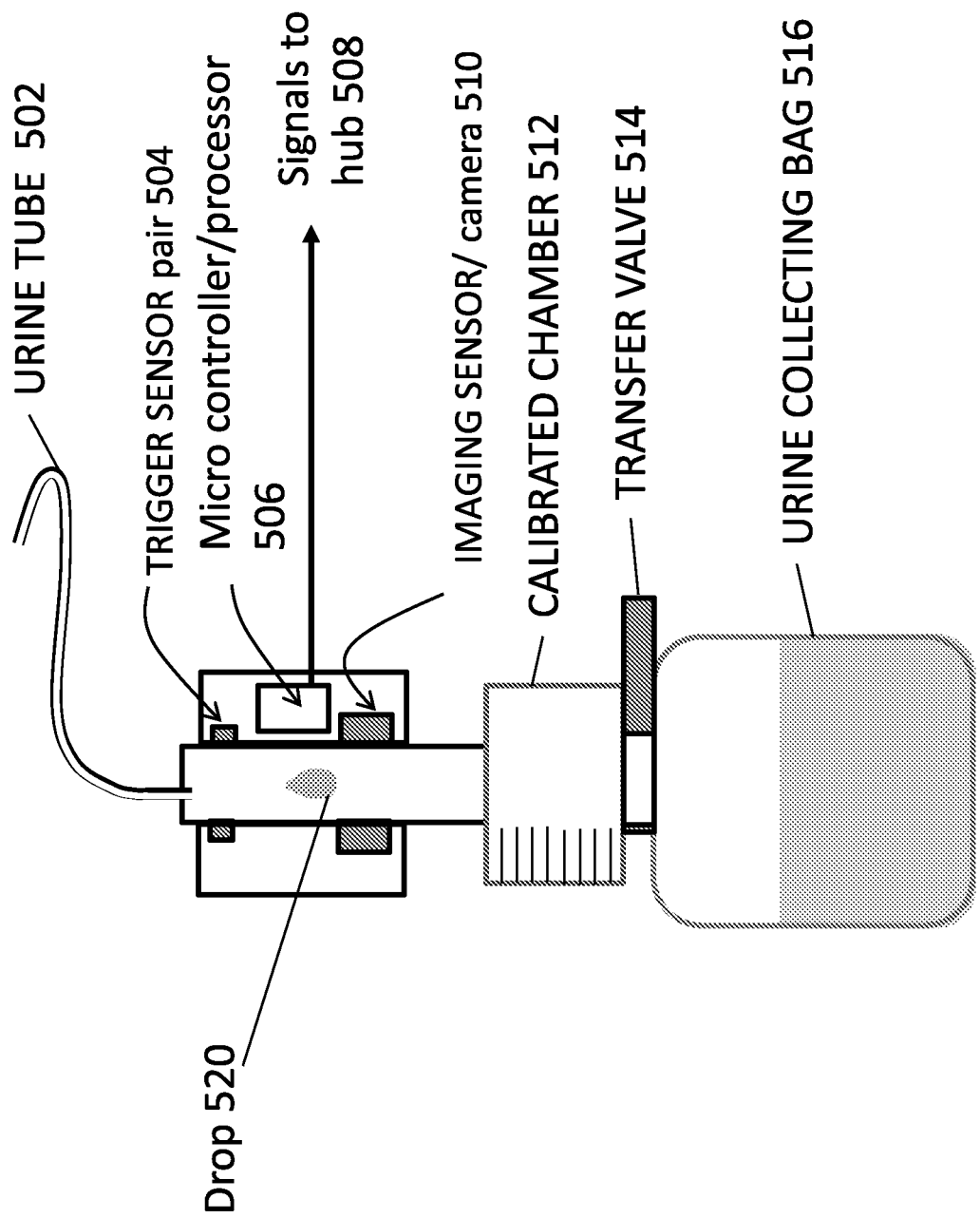
FIG. 5 is a schematic of an exemplary urine analyzer that analyzes volume of urine drops and outputs signals for calculation of the urine output flow rate, in accordance with some embodiments of the present invention.

Reference is now made to FIG. 5, which is a schematic of an exemplary urine analyzer that analyzes volume of urine drops and outputs signals for calculation of the urine output flow rate, and/or computes and outputs the urine output flow rate, in accordance with some embodiments of the present invention.

An inlet urine tube 502 receives urine outputted by the patient. A falling drop 520 triggers sensor 504 and is imaged by optical sensor (e.g., camera) 510, as described herein. A microcontroller 506 (e.g., implemented as circuitry and/or code instructions executed by one or more processors) process the captured images and/or timing signals, and outputs signals 508 to a hub and/or other computing unit for further processing and/or presentation on display. Microcontroller 506 may process and output the raw image and/or timing signals from processing by the other computing unit and/or hub. Alternatively or additionally, microcontroller 506 analyzes the images and/or timing signals and outputs the estimated drop volume and/or calculated urine output flow rate.

The drops (after being images) may be collected in a urine collection bag 516. Bag 516 (which is optionally disposable) may be replaced by shutting transfer valve 514.

Calibrated chamber 512 may be used to measure the total volume of accumulated urine over a significant period of time.

Figure 6A:
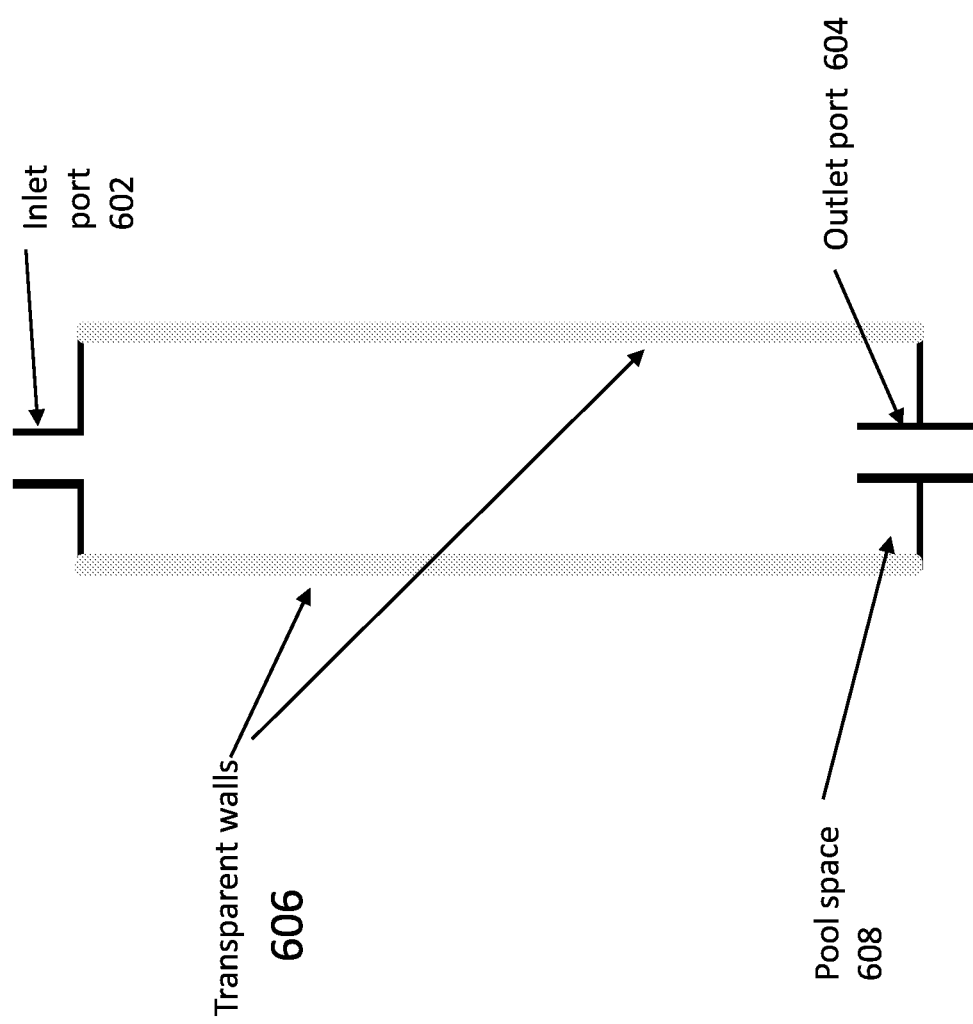
FIG. 6A is a schematic of an exemplary drip chamber and/or inspection capsule, in accordance with some embodiments of the present invention.

Reference is now made to FIG. 6A, which is a schematic of an exemplary drip chamber (e.g., 106 described with reference to FIG. 1), and/or inspection capsule (e.g., 411 described with reference to FIG. 4), in accordance with some embodiments of the present invention. An inlet port 602 receives a drop of urine. The drop of urine falls between transparent walls 606. The drops of urine accumulate within a pool space 608 at the bottom of the drip chamber (and/or inspection capsule), and leave from an outlet port 604. The drip chamber is sized and shaped to accommodate a drop falling, optionally without contacting walls 606, and having a length long enough so that flow sensor 110 and/or timing mechanism 112 are able to time the drop and/or sense the drop.

Figure 6B:
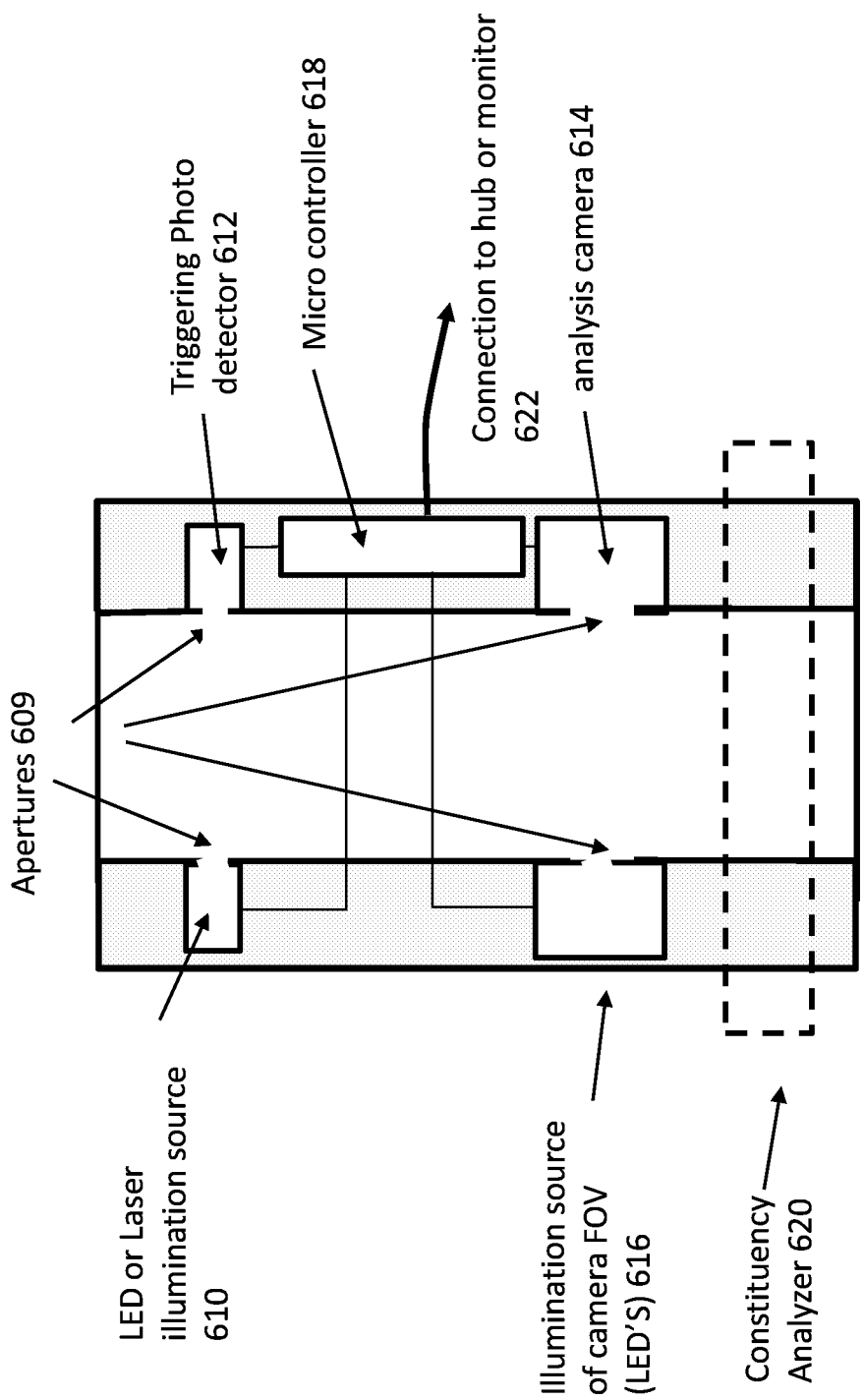
FIG. 6B is a schematic of the drip chamber and/or inspection chamber of FIG. 6A positioned to accommodate measurements performed by flow sensor and/or timing mechanism on the falling drops, in accordance with some embodiments of the present invention.

Reference is now made to FIG. 6B, which is a schematic of the drip chamber and/or inspection chamber of FIG. 6A positioned to accommodate measurements performed by flow sensor 110 and/or timing mechanism 112 on the falling drops, in accordance with some embodiments of the present invention.

The walls (i.e., 606) may include indentations (e.g., when the walls are sufficiently thick) to house flow sensor 110 and/or timing mechanism 112, and/or may include apertures 609 that transmit electromagnetic radiation (e.g., windows, when the walls are not fully transparent or at risk of becoming dirty), and/or may be sufficiently transparent such that indentations and/or apertures 609 are not required. One or more of the following components (described in detail herein) are housed in indentations of the wall and/or positioned next to apertures 609: illumination source 610 (e.g., laser, LED), detector 612 (trigged by source 610), camera having conventional focusing lens or a telecentric lens 614, and illumination source for camera 616 (e.g., LED). An optional constituency analyzer 620 (that analyzes urine constituency as described herein) may be positioned below camera 614 and/or illumination source 616 to analyze the urinary constituents of the drops. Microcontroller 618 and/or interface 622 (e.g., to an external computing unit and/or hub and/or display) may be integrated within (and/or positioned externally to) the walls of the drip chamber and/or inspection chamber.

At 208, the volume of the drop is estimated. The volume is estimated using the signal outputted by flow sensor 110 (e.g., image(s)). The urine output flow rate is calculated according to the volume of the drop and the timing signals outputted by timing mechanism 112. The volume estimation and/or the urine output flow rate may be calculated by flow code 112A executed by processor(s) 124 of computing unit 120.

Optionally, the instantaneous urine output flow rate is measured. It is noted that the instantaneous flow rate is an approximation of the instantaneous flow rate based on an estimation of the flow rate of the individual drops. The instantaneous urine output flow rate may be measured using one or two drops, based on the relative time between the two drops. The flow rate may be measured using a larger number of drops, based on the total measured time for the drops, for example, based on 3 drops, 10 drops, or 50 drops, or 100 drop, or a larger number of drops, or the number of drops falling within about 1 second, about 1 minute, about 5 minutes, about 10 minutes, or 30 minutes, or 60 minutes, or other time units. The unit basis for which the urine output flow rate may be selected according to clinical relevance, accuracy in measurement, ability to present the points on a display, and/or other factors.

Figure 7:
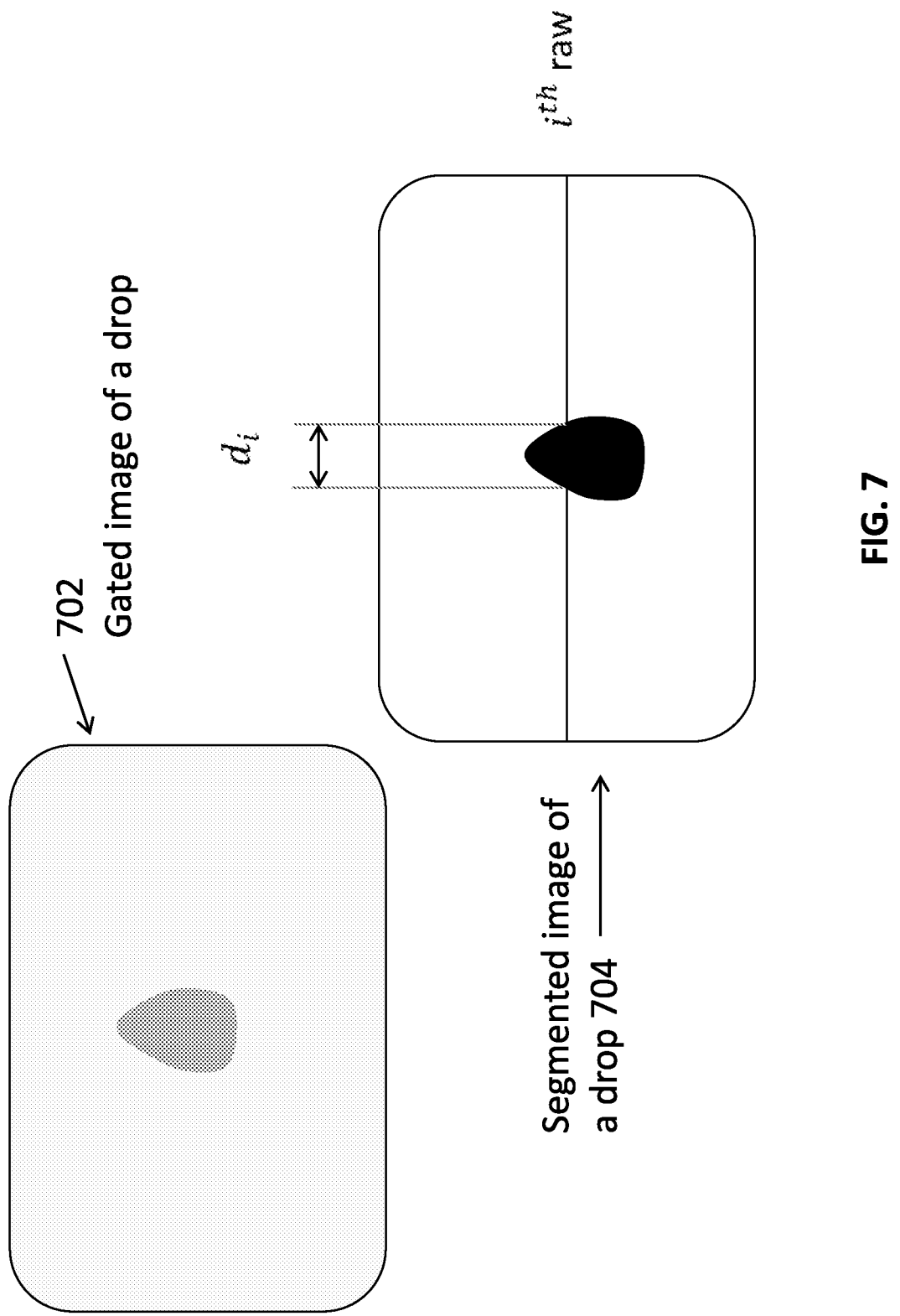
FIG. 7 is a schematic of processed drop images obtained by a sensor, in accordance with some embodiments of the present invention.

Reference is now made to FIG. 7, which is a schematic of processed drop images obtained by a sensor, in accordance with some embodiments of the present invention. Image 702 is an exemplary image as captured by the gated camera. Image 702 may be processed (e.g., using image processing code instructions executed by one or more processors) to segment the image of the drop, shown as image 704. For example, image 702 may be processed using a binary filter, to create a binary image 704, where black represents the volume of the drop. Optionally, one or more images are captured for each drop, for example, 2, 3, 5, or more images. The best image may be selected, or multiple images may be analyzed per drop with the results averaged.

$d_i$ denotes a measurement of a horizontal cross section (or slice) obtained from image 704, for example, using image processing methods.

The volume of one or more drops (i.e., accumulated total volume of the drops) over a unit of time may be calculated using the equation:

$$V_{drop} = K\Sigma_1^n d_i^2$$

where:

$V_{drop}$ denotes the volume of the drop, or accumulated volume of drops (e.g., in milliliters), K denotes a calibration constant dependent on the camera scaling geometry, n denotes the number of drops over the unit of time, $d_i$ is as shown with reference to image 704, and described above.

Alternatively or additionally, the above volume equation may be used to estimate the volume of each drop, using multiple images acquired of each drop, and multiple cross sections areas calculated for each drop. Each image may be analyzed to calculate the cross sectional area for a different part of the drop. Each cross section may be estimated to have a uniform on interpolated thickness estimated between sequential cross sections. Summing the volume of the cross sectional volumes provides the total volume of the drop. Additional details may be found, for example, with reference to WO2016084080.

The urine output flow rate may be calculated as the product of the drip rate multiplied by the average drop volume, calculated over a pre-determined time interval. The drip rate may be determined based on counting the number of drops, for example, using flow sensor 110, timing mechanism 112, or another sensor that detects and counts drops. The average drop volume may be calculated, for example, based on a sample of drops (e.g., random sample, every predefined number of drops, every predefined time interval, and the like), a set or all drops, or other methods as described herein. The time interval may be preset, and/or defined by a user, for example, about 10 minutes, or 30 minutes, or 60 minutes, or other time intervals.

The urine output flow rate may be calculated based on adding the volume of a sequence of individual drops over the predetermined time interval, or another time during which the sequence of drops were added.

The urine output flow rate may be calculated using the equation:

$$\text{flow rate} = N \times V_{drop}$$

Where:

N denotes the number of drops per unit of time used to determine the accumulated volume of drops (e.g., number of drops per hour, or single drop per unit of time, or multiple drops per unit of time), $V_{drop}$ is the total average volume of the drops over the unit of time.

Optionally, a trend is indentified based on multiple urine output flow rate points (e.g., calculated as described above). The trend is indicative of a decrease or increase in the urine output flow rate. For example, an upwards trend is indicative that the patient is producing more urine per unit of time. For example, a downward trend is indicative that the patient is producing less urine per unit of time. The trend is analyzed based on a predefine tolerance range that indicates a tolerated range of values for the patient, which is indicative of a safe and/or healthy and/or adequate urine output of the patient. Optionally, the identified trend is indicative of acute kidney injury (AKI).

An indication of the detected AKI may be presented on the GUI and/or provided as an alert (as described herein). The trend indicative of AKI may be identified, for example, based on the AKI definition as described with reference to: Section 2: AKI Definition, *Kidney International Supplements* (2012) 2, 19-36, Ralib, Azrina Md, et al. "The urine output definition of acute kidney injury is too liberal." Critical care 17.3 (2013): 1, and Labib, Mary, et al. "Volume management in the critically ill patient with acute kidney injury." Critical care research and practice 2013 (2013), all of which are incorporated herein by reference in their entirety.

For example, urine output below the range may be indicative of, for example, acute renal failure (ARF). For example, urine output above the range may be indicative of, for example, post obstructive dieresis (POD). Optionally, the trend is predictive of a future urine flow rate value that falls outside of the predefined tolerance range. For example, in about 6 hours the patient is predicted to have a decreased urine output below the lower limit, which may be suggestive of, for example, that the patient is developing ARF. In another example, in about 4 hours the patient is predicted to have an increased urine output above the upper limit, which may be suggest of, for example, that the patient is developing POD.

Optionally, an alert is generated when the urine output flow rate is actually outside the tolerance range, or is predicted to fall outside the tolerance range in the near future (i.e., the next few hours). The alert may be transmitted as an instant message to a Smartphone of a healthcare provider (e.g., nurse, on call physician), presented on the GUI presenting the trend, transmitted and presented on another computing device performing monitoring of the patient, or other implementations.

Optionally, the trend is identified according to a least square regression analysis conducted using a sliding window of a predefined number of urine output flow rate measurements. For example, y(0), y(1), y(i), ... y(n), y(n+1) denote the calculated urine output flow rates, optionally calculated at predefined time intervals, for example, every 30 minutes, or every hour, or other units of time. z(i)=ax(i)+b denotes the identified trend line for the calculated urine outflow rates from y(0) to y(n) (i.e., the trend is calculated for a sliding window of size n, optionally for the last n samples, where Δ denotes the time interval between consecutive samples).

The following equations are solved:

$$J(a, b) = \sum_1^n [y(i) - z(i)]^2$$

$$\frac{\partial J}{\partial a} = 0 \quad \frac{\partial J}{\partial b} = 0$$

$$a = \frac{\sum_1^n y(i)[i - 0.5(n+1)]}{\left[\sum_1^n i^2\right] - n(n+1)}$$

At 210, one or more constituent signals are generated based on an analysis conducted on the urine flowing within the drip chamber. The constituent signals are indicative of one or more constituents within the urine. The constituent signals are generated for each constituent being analyzed.

Exemplary constituents being detected include one or more of: organic compounds, inorganic compounds, cells (red blood cells, white blood cells), parts of cells (i.e., from burst cells, for example, hemoglobin), proteins (optionally per type of protein, for example, protein size), urea, chloride, sodium, potassium, ions, creatinine, and glucose.

The concentration may be detected for each constituent. Alternatively, the presence of an amount of constituent (e.g., greater than zero, or greater than a threshold) is detected, for example, the presence of blood in the urine, the presence of ketones in the urine, and the presence of glucose in the urine.

Alternatively or additionally, the constituents are detects as a group, without necessarily considering the composition, for example, the urine osmolality may be estimated. As used herein, the term constituent may include the measurement of urine osmolality or other measurement based on multiple components.

The drop of urine or a sequence of multiple drops is analyzed prior to urine drop entering a urine collection bag in fluid communication with the outlet, optionally while the urine drop is within the drip chamber.

The drop of urine is analyzed to identify the constituents after being analyzed for calculation of the volume of the drop (i.e., in implementations that measure both the urine flow rate and the constituents).

Figure 8:
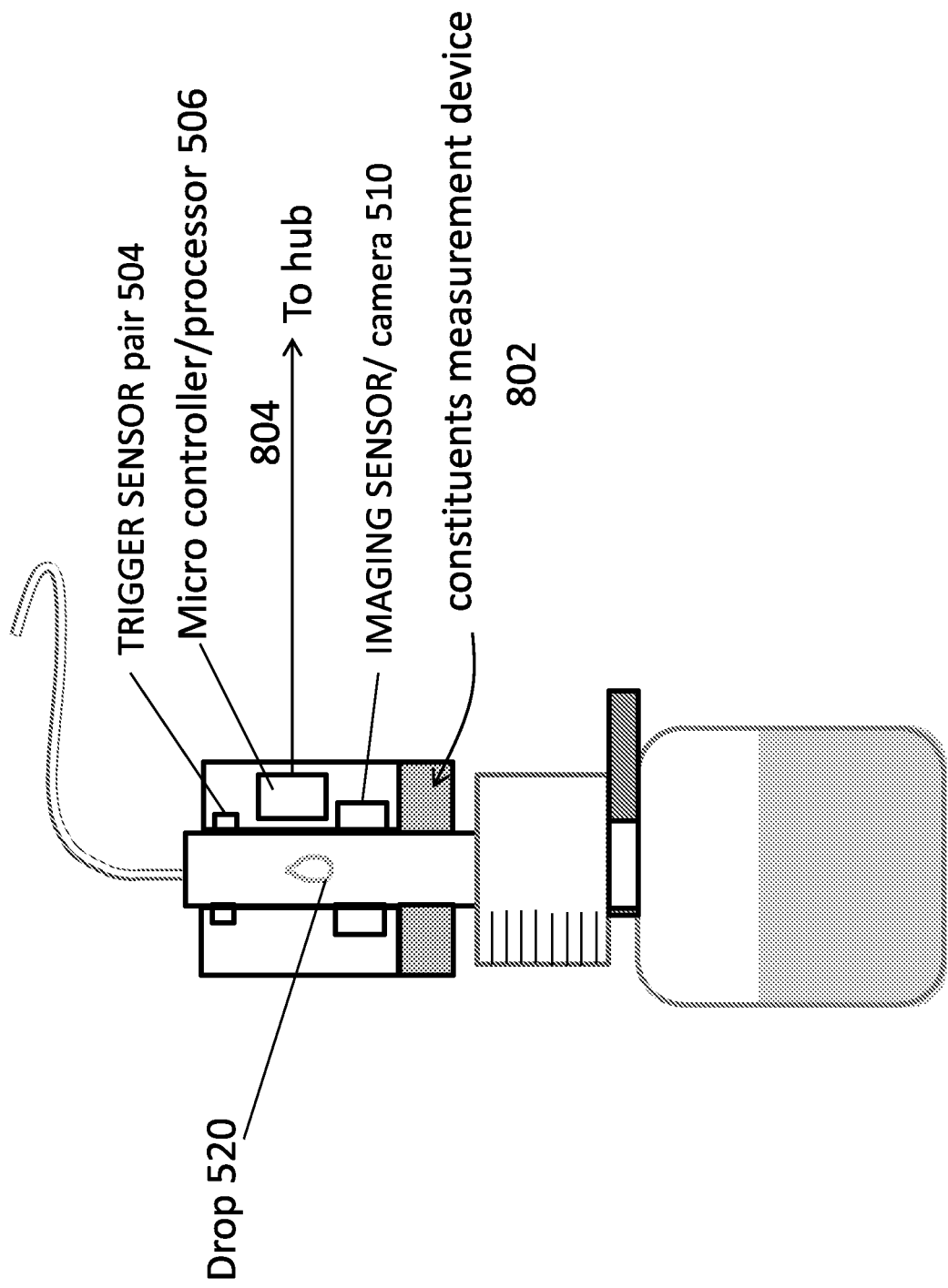
FIG. 8 is a schematic of the exemplary urine analyzer device described with reference to FIG. 5, including a constituent measurement device that measures the constituents in the urine, in accordance with some embodiments of the present invention.

Reference is now made to FIG. 8, which is a schematic of the exemplary urine analyzer device described with reference to FIG. 5, including a constituent measurement device 802 that measures the constituents in the urine, in accordance with some embodiments of the present invention. Constituent measurement device 802 may correspond to constituent measuring elements(s) 116 described with reference to FIG. 1. Constituent measurement device 802 is positioned below trigger sensor 504 and imaging sensor 510 (i.e., below flow sensor 110), to analyze drops 520 sensed for calculation of the volume of the drop. It is noted that constituent measurement device 802 is located below trigger sensor 504 and imaging sensor 510 (i.e., below flow sensor 110) since the constituent analysis may affect the ability to calculate the volume of the urine, for example, by absorbing the urine during the analysis process. Signals 804 processed by processor 506 indicative of the concentration and/or presence of one or more constituents may be transmitted to an external computing unit, a hub, and/or a display, as described herein.

The falling urine drops fall on respective constituent measuring elements 116 that each sequentially perform measurements of respective urine constituents for each respective drops, for example, each drop of urine is analyze for one respective constituent. Multiple constituents are analyzed by independently analyzing multiple individual drops. A constituent signal indicative of the respective urine constituent of the respective drop is generated and analyzed, as described herein.

Figure 9:
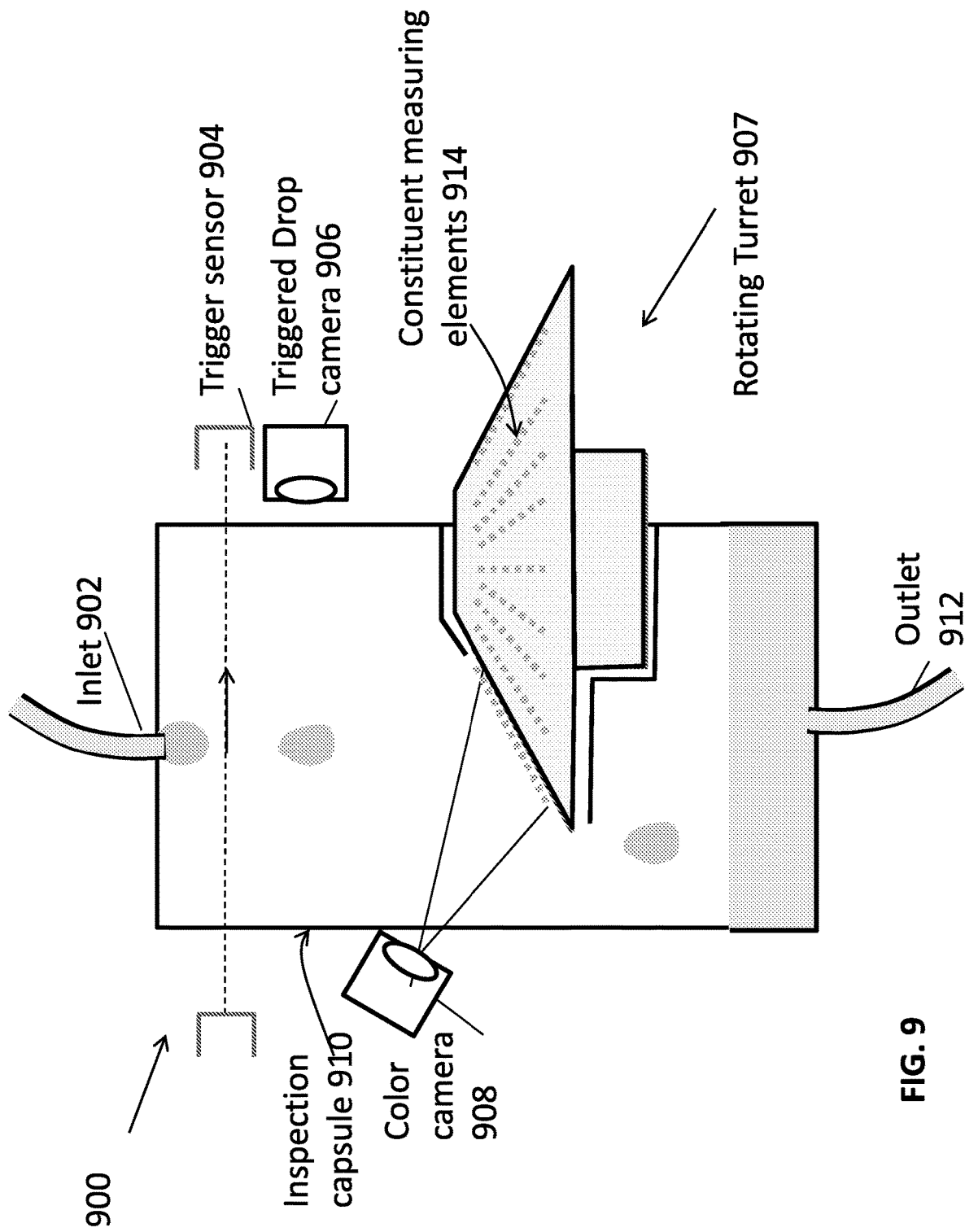
FIG. 9 is a schematic of an implementation of a rotating apparatus that rotates to contact each constituent measuring element with a different drop of urine, in accordance with some embodiments of the present invention.

Reference is now made to FIG. 9, which is a schematic of an implementation of constituent measuring elements 116 based on a rotating apparatus 900 that rotates to contact each constituent measuring element 116 with a different drop of urine, in accordance with some embodiments of the present invention.

Urine drops are received from an inlet 902. Falling urine drops trigger sensor 904, which may be implemented, for example, as a pair of an electromagnetic source (e.g., light) and a receiving sensor. It is noted that sensor 904 may be implemented for example, as sensor 504 of FIG. 5. Sensor 904 may trigger camera 906 for imaging the drop for calculation of the drop volume, triggering rotating turret 908.

Turret 907 includes constituent measuring elements 914 arranged on a surface of a rotating element, which may be positioned at an angle relative to the falling drop (i.e. to allow the drop to spread along the length of each element 914), or may be positioned flat (i.e., horizontally) with drop(s) dripped individually to each constituent measuring element 914. The horizontal orientation may avoid potential interactions when a single drop passes across multiple elements 914, by preventing movement of the drops that fell on a certain element 914 from flowing to another neighboring element 914. Each of constituent measuring element 914 estimates a concentration (and/or presence) of a different urine constituent in a drop of urine.

Turret 907 turns a predefined amount (i.e., arc length, rotation fraction) to expose a new constituent measuring element 914 to the new falling drop. The rotation of turret 907 may be triggered by sensor 904, and/or may be triggered based on a predefined time intervals corresponding to the calculated urine flow rate. Turret 907 may be controlled by a motor (e.g., servomotor) coupled to sensor 904, and/or controlled by a controller.

Each constituent measuring element 914 may be implemented as a respective lab-on-chip (LOC) (e.g., solid state) designed to be sensitive to estimate a concentration (or presence) of a different respective urine constituent. Each LOC outputs a signal indicative of the measured concentration (or presence) of the respective urine constituent). Each signal is analyzed (e.g., by constituent code 122B) to calculate the concentration of the respective constituent of the respective LOC.

In another exemplary implementation, each constituent measuring element 914 includes an impregnated strip media that changes to a different color according to the concentration (or presence) of the respective constituent. Device 900 may include a color camera 908 (e.g., red green blue (RGB) camera, or multi-spectral imager) sized and/or positioned to sense the changed color of each respective constituent measuring element 914. Camera 908 may capture an image of the current constituent measuring element 914 at each rotation for a pre-determined amount of urine drops. Camera 908 outputs a signal indicative of the sensed changed color. The signal is analyzed (e.g., by constituent code 122B) to calculate the concentration of the respective constituent corresponding to the sensed changed color.

Rotating turret 907 may be controlled to expose different regions of the same constituent measuring element 914 to new drops of urine, for example by tilting the angle of turret 907, and/or backwards-forwards positioning and/or up-down positioning of turret 907. For example, each element 914 may include multiple regions to sense multiple urine drops. After each rotation of turret 907, turret 907 may be repositioned to expose a new row of regions to the drops. Each turret 907 may be used to analyze a large number of drops.

Optionally, a rinse element(s) and/or dryer element(s) (e.g., heater, air blower) may be positioned to apply a rinse cycle and/or a dry cycle to constituent measuring elements 914 to provide for re-use with new drops.

Turret 907 may be disposable, and/or replaceable.

Urine remaining after the analysis falls down, and may exit from an outlet 912, for example, into a urine collection bag.

Referring now back to block 210 of FIG. 2, alternatively or additionally, the constituency of the drop of urine is analyzed based on spectral analysis.

Figure 10:
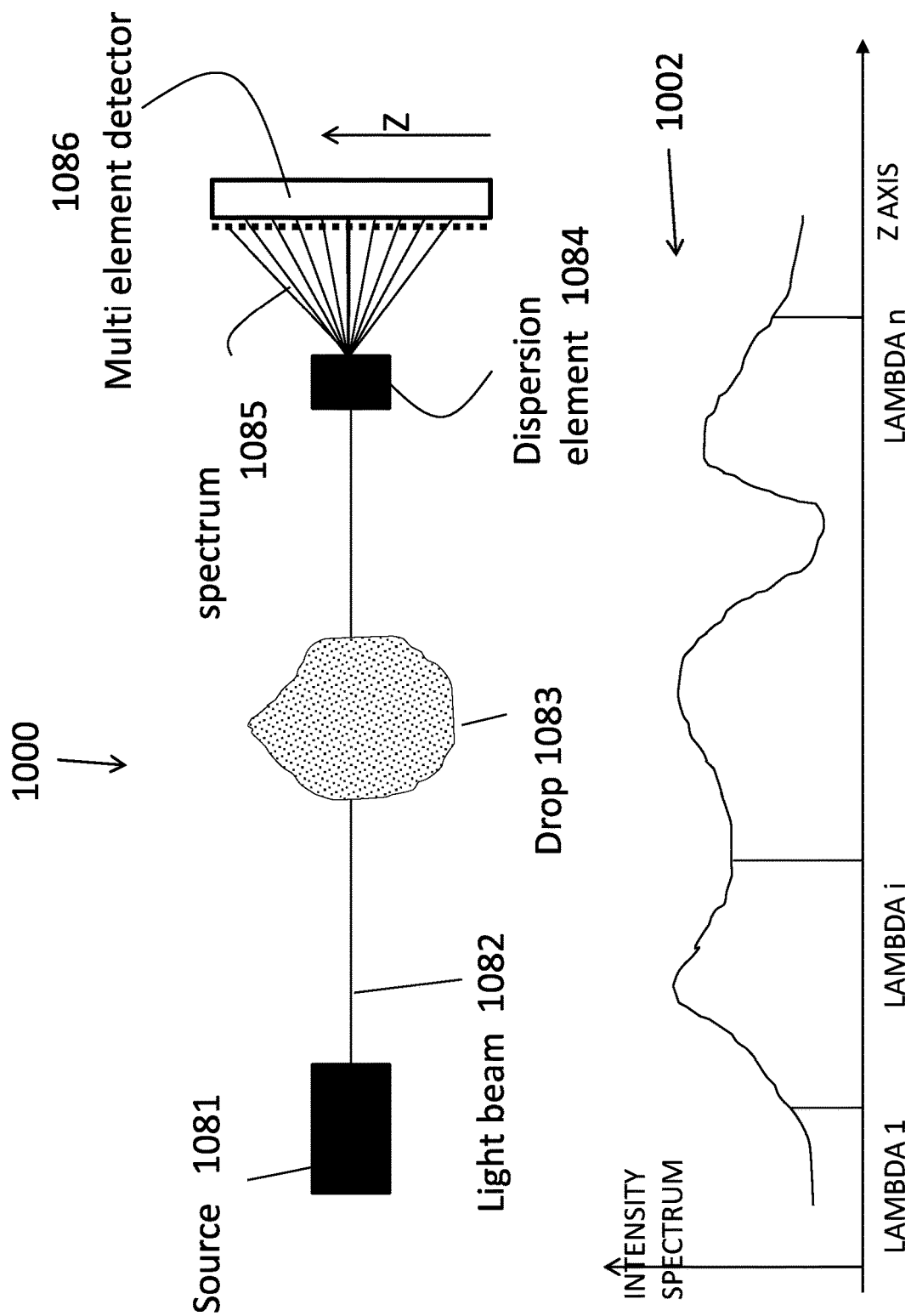
FIG. 10 is a schematic depicting components of a spectral analysis system for measuring the constituent(s) of urine, and a sample spectral output, in accordance with some embodiments of the present invention.

Reference is now made to FIG. 10, which is a schematic depicting components of a spectral analysis system 1000 for measuring the constituent(s) of urine, and a sample spectral output 1002, in accordance with some embodiments of the present invention. System 1000 may simultaneously measure multiple urine constituents within the same drop 1083. Spectral analysis system 1000 may implemented within constituent measurement device 802 (i.e., as constituent measuring element 116) below flow sensor 110 (or other sensor implementations for calculating of urine drop volume).

A light source 1081 (e.g., LED, light bulb, multi-colored laser) generates a light 1082 that is directed towards drop of urine 1083 (or portion of the drop). A spectral dispersion element 1084 disperses the light that passed through drop 1083 to create a spectrum 1085. A multi element detector 1086 senses spectrum 1085 (i.e., the dispersed light). Constituent code 122B instructions when executed by processing unit 120, analyze spectrogram 1085 to identify concentration of one or more urine constituent within drop of urine 1083.

Graph 1002 is an exemplary spectral intensity graph generated based on output of multi element detector 1086. Each $lambda_i$ denotes a different urine constituent. The spectral intensity may be indicative of the relative concentration of the respective constituent.

Alternatively, in another implementation, source 1081 is a tunable source that is adjustable to emit a selected wavelength (or sub-range) from a range of wavelengths of light. A single detector may be implemented instead of multi element detector 1086. Source 1081 may be sequentially turned to different wavelengths for measurement by the single detector. The signals may be sequentially analyzed to identify each constituent corresponding to the selected wavelength.

Figure 11:
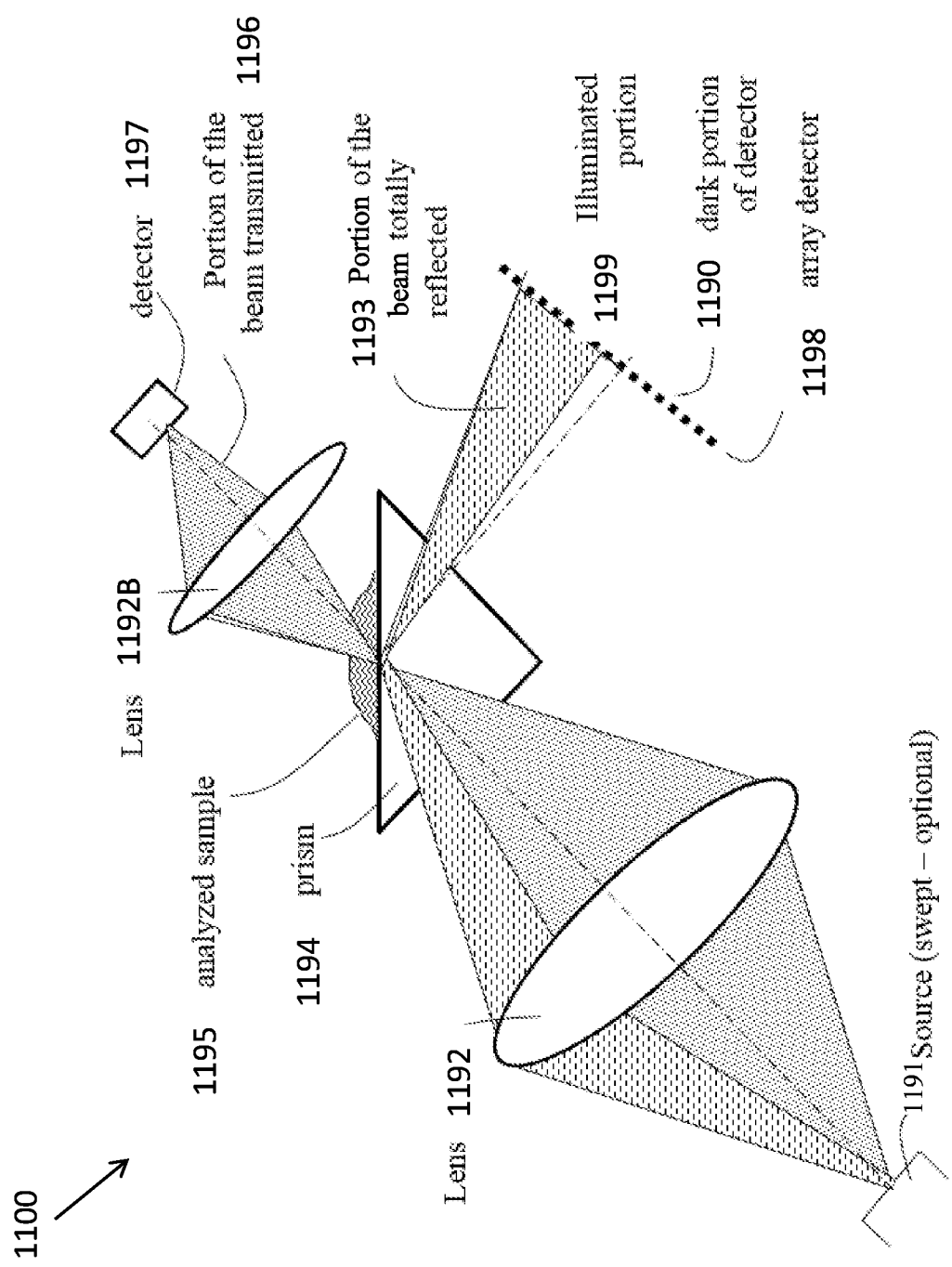
FIG. 11 is a schematic of an exemplary implementation of a constituent analyzer based on spectral analysis, in accordance with some embodiments of the present invention.

Reference is now made to FIG. 11, which is a schematic of an exemplary implementation of a constituent analyzer 1100 based on spectral analysis (as described with reference to FIG. 10), in accordance with some embodiments of the present invention. Constituent analyzer 1100 estimates, in real time, the osmolarity and/or osmolality and/or the spectral content (which may be used to identify concentration of individual constituents) of one or more drops of the patient.

Light source 1191 may be a sweeping source. Light produced by source 1191 is directed by lens 1192 to analyzed sample 1195 (i.e., urine drop) positioned on a prism 1194. Urine drops may be directed to prism 1194 (i.e., spectral dispersion element) by a drip directing mechanism, for example, one or more drops may be directed for analysis at selected time intervals, for example every 30 minute, or every hour, or based on a manual selection, or other periods of time.

Optionally, prism 1194 is a TIR prism that splits the light to two portions. A first portion of the light 1193 is totally (or mostly) reflected (i.e., does NOT pass through urine 1195). Light 1193 is directed to an illuminated portion 1199 of an array detector 1198. It is noted that certain portions 1199 of array detector 1198 are illuminated, while other dark portions 1190 remain un-illuminated. Portion of light 1193 reaching illuminated portion 1199 of detector 1198 is based on rays arriving at a certain critical angle that are reflected by prism 1194. Portion of light 1193 reaching illuminated portion 1199 is association (e.g., a function of) the refractive index of urine 1195. The refractive index is a function of multiple constituents in urine 1195, also termed osmolarity. The intensity and/or location(s) of illuminated portion 1199 (and/or the location(s) of dark portion 1190) relative to array detector 1198 may be analyzed to estimate the osmolarity of the urine constituents, for example, by constituent code 122B.

A second portion of the light 1196 passes through urine 1195. The passed light is directed by another lens 1192B to another detector 1197, optionally that includes a single detection element. When source 1191 is swept as a function of time, the output of detector 1197 as a function of time may be graphed as the optical spectrum of urine 1195, and analyzed (e.g., by constituent code 122B) to calculate one or more constituents of the urine (i.e., according to the wavelength(s) outputted by source 1191).

Figure 12:
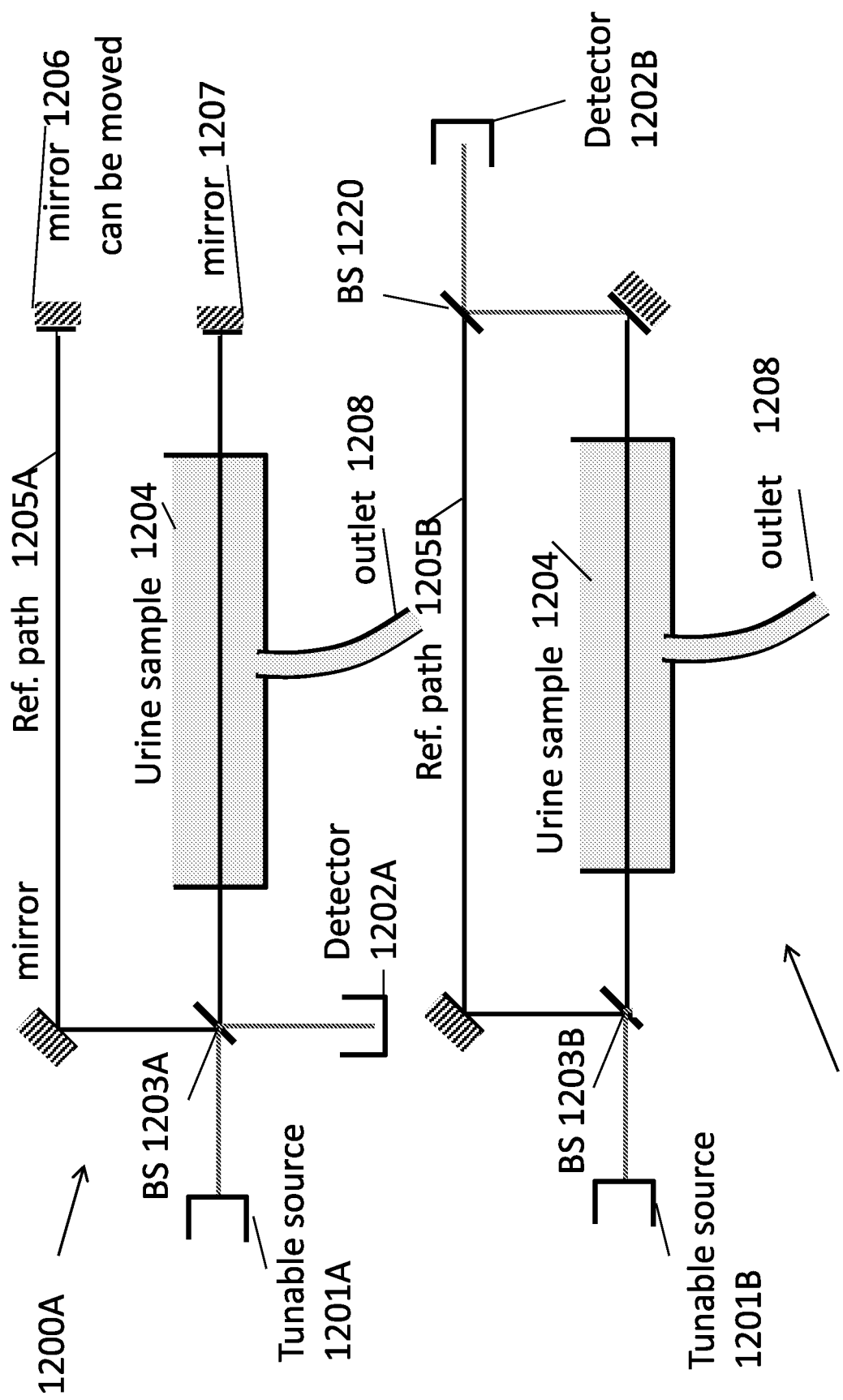
FIG. 12 is a schematic of another exemplary implementation of the constituent analyzers based on spectral analysis, in accordance with some embodiments of the present invention.

Reference is now made to FIG. 12, which is a schematic of another exemplary implementation of constituent analyzers 1200A-B based on spectral analysis (as described with reference to FIG. 10), in accordance with some embodiments of the present invention.

Constituent analyzers 1200A-B are based on an interferometer design. Analyzer 1200A is based on a Michelson interferometer design, and analyzer 1200B is based on a Mach-Zender interferometer design. Analyzers 1200A-B include a tunable source 1201A-B capable of emitting a range of wavelengths, for example, a vertical-external-cavity surface-emitting-laser (VECSEL).

With reference to analyzer 1200A, a beam splitter (BS) 1203A splits the beam generated by tunable source 1201A to a first reference path 1205A that is reflected back to beam splitter 1203A by a mirror 1206 that is optionally adjustable. Beam splitter 1203A splits the beam generated by tunable source 1201A to a second path that passed through a urine sample 1204, and is reflected back to beam splitter 1203A through urine sample 1204 by another mirror 1207. Beam splitter 1203A combines the beams reflected by mirrors 1206 and 1207, and directs the combined beams to a detector 1202 that outputs a signal that may be analyzed to estimate the concentration of constituents in the urine (e.g., osmolarity and/or osmolality) by constituent code 122B executed by processing unit 120.

With reference to analyzer 1200A, a BS 1203B splits the beam generated by tunable source 1201B to a first reference path 1205B and a second path that passes through urine sample 1204. Path 1205B and path through urine sample 1204 are combined by another beam splitter 1220 for sensing by a detector 1202B that outputs a signal that may be analyzed to estimate the concentration of constituents in the urine (e.g., osmolarity and/or osmolality) by constituent code 122B executed by processing unit 120.

It is noted that additional mirrors may be used to direct the beams of light, for example, as shown in FIG. 12.

Urine sample 1204 may be stored within a transparent (or partially transparent) chamber positioned within drip chamber 106. The transparent chamber is designed to remain in a state filled with urine, optionally without air residing in the transparent chamber. Optionally, each new drop of urine displaces a corresponding volume from the chamber (e.g., out through outlet 1208), maintaining the chamber in a filled state. The chamber is position such that the light along the path through urine sample 1204 passes through walls of the transparent chamber and through the urine sample 1204 within the transparent chamber.

It is noted that different implementations described herein may be simultaneously implemented in the same device, for example, analyzer 1200A described with reference to FIG. 12 may be installed to measure the urine osmolarity and/or osmolality, and device 900 described with reference to FIG. 9 may be installed to measure the concentration of certain urine constituents.

At 212, signals outputted as described with reference to block 210 are analyzed by constituent code 122B executed by processor(s) 124 to estimate the concentration of one or more urine constituents (i.e., concentration per constituent), the presence of one or more urine constituents (i.e., the presence of each constituent) optionally above a threshold (e.g., zero, a concentration threshold), and/or the osmolarity and/or osmolality of the urine.

As used herein, the term concentration (of urinary constituents) sometimes refers to one or more of the following: the concentration of one or more urine constituents (i.e., concentration per constituent), the presence of one or more urine constituents (i.e., the presence of each constituent) optionally above a threshold (e.g., zero, a concentration threshold), and/or the osmolarity and/or osmolality of the urine.

Constituent code 122B may analyze spectral intensity graph 1002 (described with reference to FIG. 10) generated based on output of multi element detector 1086. Each lambda$_i$ denotes a different urine constituent. The spectral intensity may be indicative of the relative concentration of the respective constituent.

Figure 13:
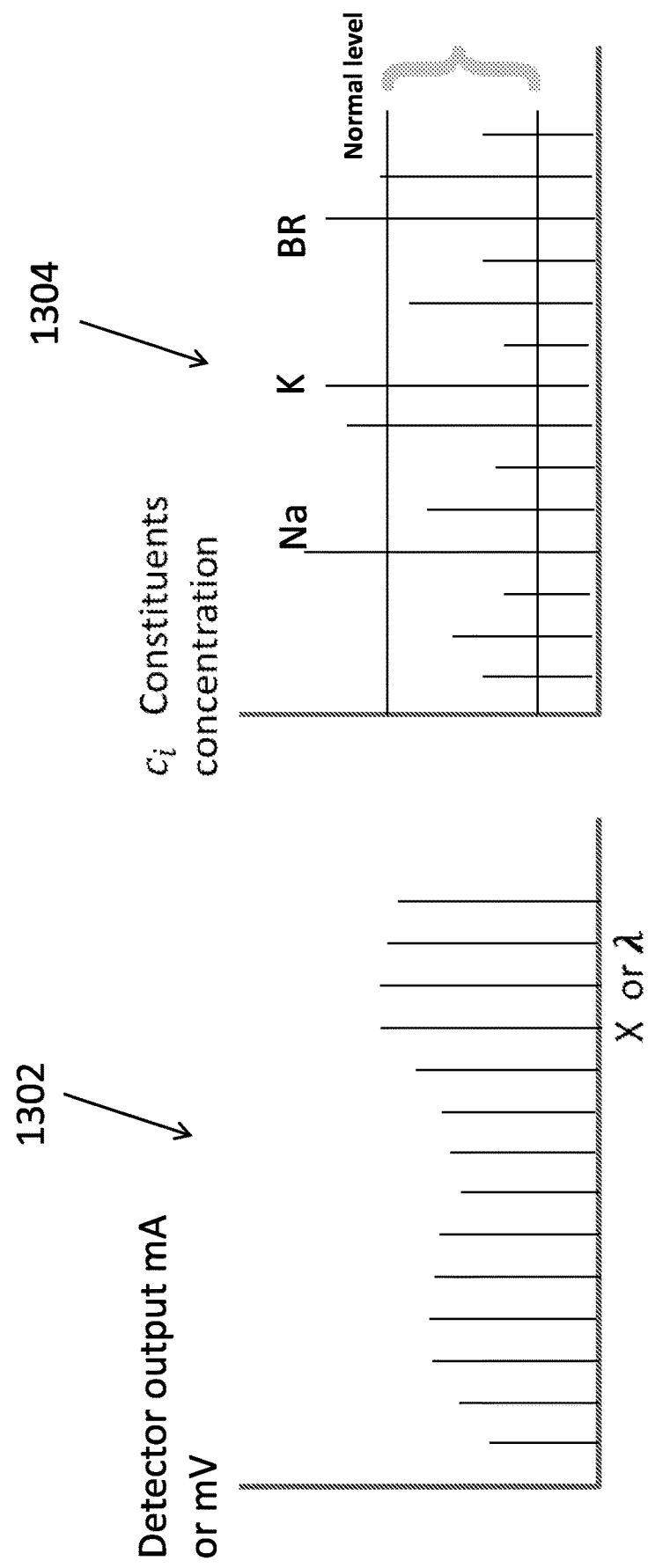
FIG. 13 includes signals and/or graphs used to extract concentrations of one or more urinary constituents from the signal(s) outputted by urine analyzers, in accordance with some embodiments of the present invention.

Alternatively or additionally, constituent code 122B may analyze the combined spectral signals outputted by analyzers 1200A-B described with reference to FIG. 12. Reference is now made to FIG. 13, which includes signals and/or graphs used to extract concentrations of one or more urinary constituents from the signal(s) outputted by analyzers 1200A-B, in accordance with some embodiments of the present invention.

Graph 1302 denotes the signal outputted by detector 1202A-B described with reference to FIG. 12. The intensity of the signal (e.g., in milliamps (mA) or millivolt (mV)) may be plotted as a function of wavelength, and/or position along a detector array. Graph 1304 denotes an analysis of the signal of graph 1302, to identify constituents with a higher concentration than a normal level. For example, in the example shown, Na, K, and Br have elevated concentration in the urine.

The signal may be analyzed, for example, based on a least square minimization method to identify with a corresponding point of a calibration curve, a predefined function and/or template representing empirically derived measurements (and/or mathematically calculated estimates based on a model).

Figure 14:
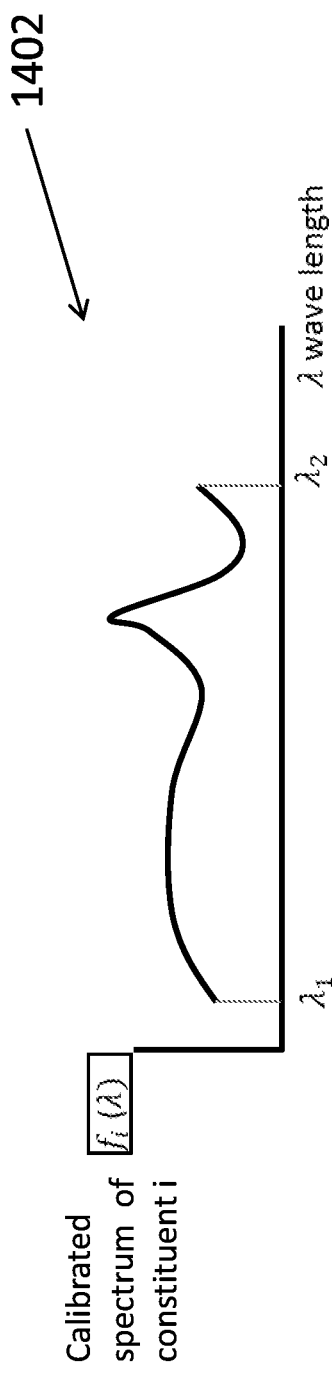
FIG. 14 is an example of a calibration curve for estimating concentration of a certain urinary constituent, in accordance with some embodiments of the present invention.

Reference is now made to FIG. 14, which is an example of a calibration curve 1402 for estimating concentration of a certain urinary constituent, in accordance with some embodiments of the present invention. Calibration curve 1402 denotes a calibrated spectrum of intensity as a function of wavelength for a certain urinary constituent (or a certain combination of constituents). Curve 1402 may be created based on empirical measurements, and/or based on a mathematical model.

When the sensor (any relevant implementation described herein) outputs an intensity for a wavelength λ, the concentration of the corresponding urinary constituent (denoted as $c_i$) may be estimated using the calibration curve (denoted as $f_i$) by minimization of a least squares function mathematically represented as:

$$I = \int \left[ g(\lambda) - \sum_1^n c_i f_i(\lambda) \right]^2 d\lambda \text{ from } \lambda_1 \text{ to } \lambda_2$$

$$\frac{dJ}{dc_i} = 0 \,\, \forall \,\, | \, 1 \ldots n$$

And assume no correlation between the constituents spectra i.e. $\int_{\lambda_1}^{\lambda_n} f_i(\lambda) f_j(\lambda) d(\lambda)$ for $i \neq j$ $$\boxed{c_i = \frac{f_g(\lambda) f_i(\lambda) d\lambda}{\int f_i^2(\lambda) d\lambda}}$$

At 214, the calculated urinary flow rate and/or the estimated concentration of urinary constituent(s) is presented on a display (e.g., user interface 128), optionally within a GUI.

Optionally, as each new measurement is performed in real-time based on urine drops as they are released from the body of the patient, the new measurements are dynamically plotted on the GUI. The trend may be updated based on the new measurement, optionally by sliding the calculation window to include the new measurement (and exclude the oldest measurement). A trend line may be plotted on the GUI to visually indicate the future prediction of the values.

The trend may be calculated for the urine flow rate, for the measured urine osmolality and/or osmolarity, the presence of one or more certain urinary constituents (e.g., above zero or another concentration threshold), and/or the concentration of one or more certain urinary constituents.

Figure 15:
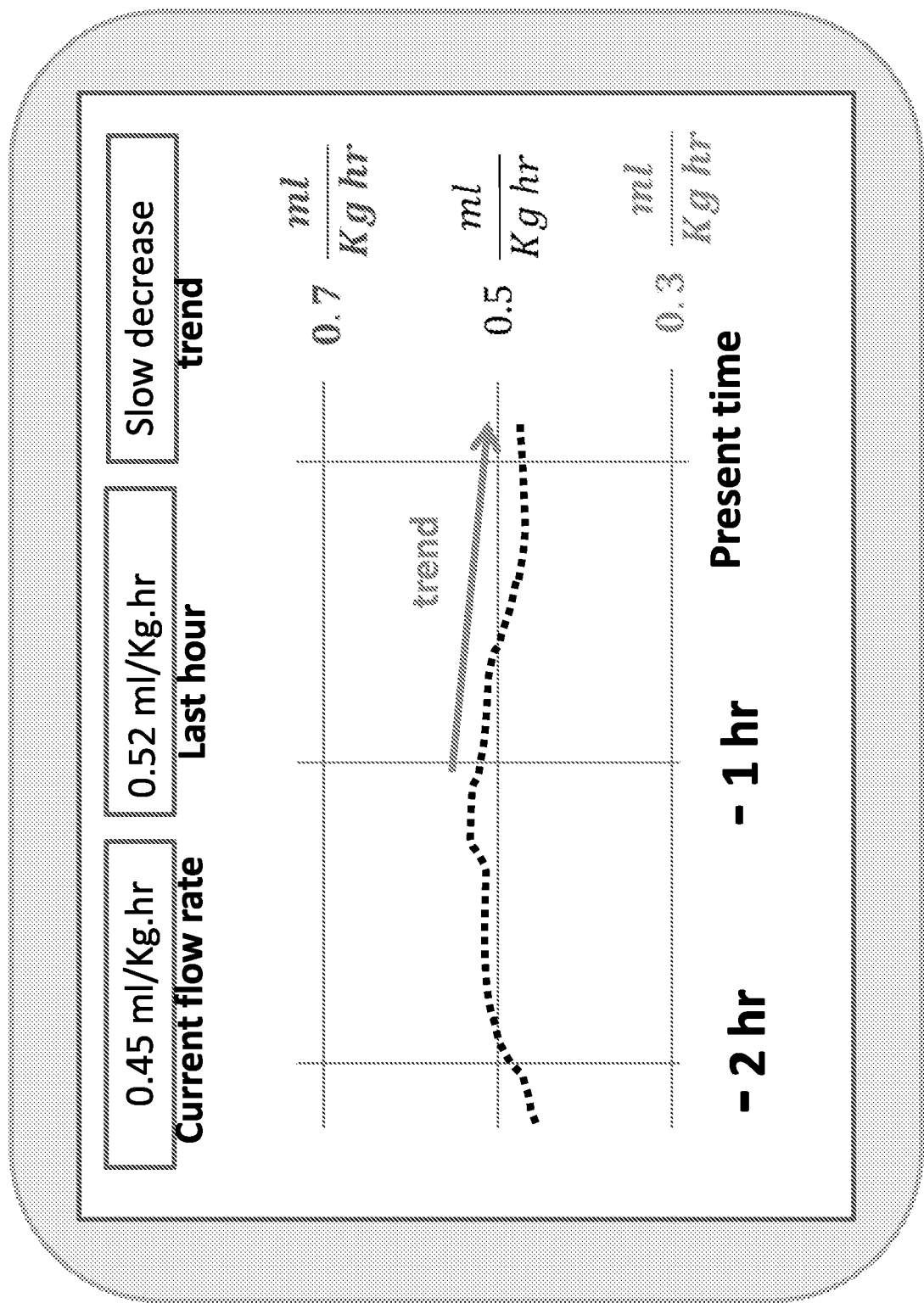
FIG. 15 is a schematic of an exemplary GUI presented on a display indicating the measured urine output flow rates, in accordance with some embodiments of the present invention.

Reference is now made to FIG. 15, which is a schematic of an exemplary GUI presented on a display indicating the measured urine output flow rates, in accordance with some embodiments of the present invention.

In the example GUI, the current (i.e., instantaneous) flow rate is measured as 0.45 ml/Kg*hour, the average flow rate (e.g., based on an average of the measurements and/or accumulated calculated volume) for the last hour is measured as 0.52 ml/Kg*hour. The calculated trend line is indicating that the urine output flow rate is decreasing. No prediction of passing the lower value of the same range (0.3 mg/Kg*hour) is made.

At 216, an alert is generated. The alert may be generated according to a set-of-rules, a function, machine learning method, artificial intelligent, or other prediction method (that may be stored in data repository 126). For example, the alert may be generated when the instantaneous urine output flow rate is out of the safe range for the patient, when the trend is indicating that the urine output flow rate is predicted to fall out of the safe range in a predefine time (e.g., in 1-2 hours), when certain constituents are detected in the urine (e.g., blood, ketones, glucose), when the osmolality and/or osmolarity of the urine is out of a predefined range (or trending out of the range), and/or when the concentration of one or more urinary constituents are out of a predefined range (or trending out of the range).

The alert may be generated, for example, as a flashing message on the GUI, as a text message transmitted to a smartphone of a healthcare provider, as a beep and message window opening up on a display at a nurse's monitoring station, or other implementations.

Figure 16:
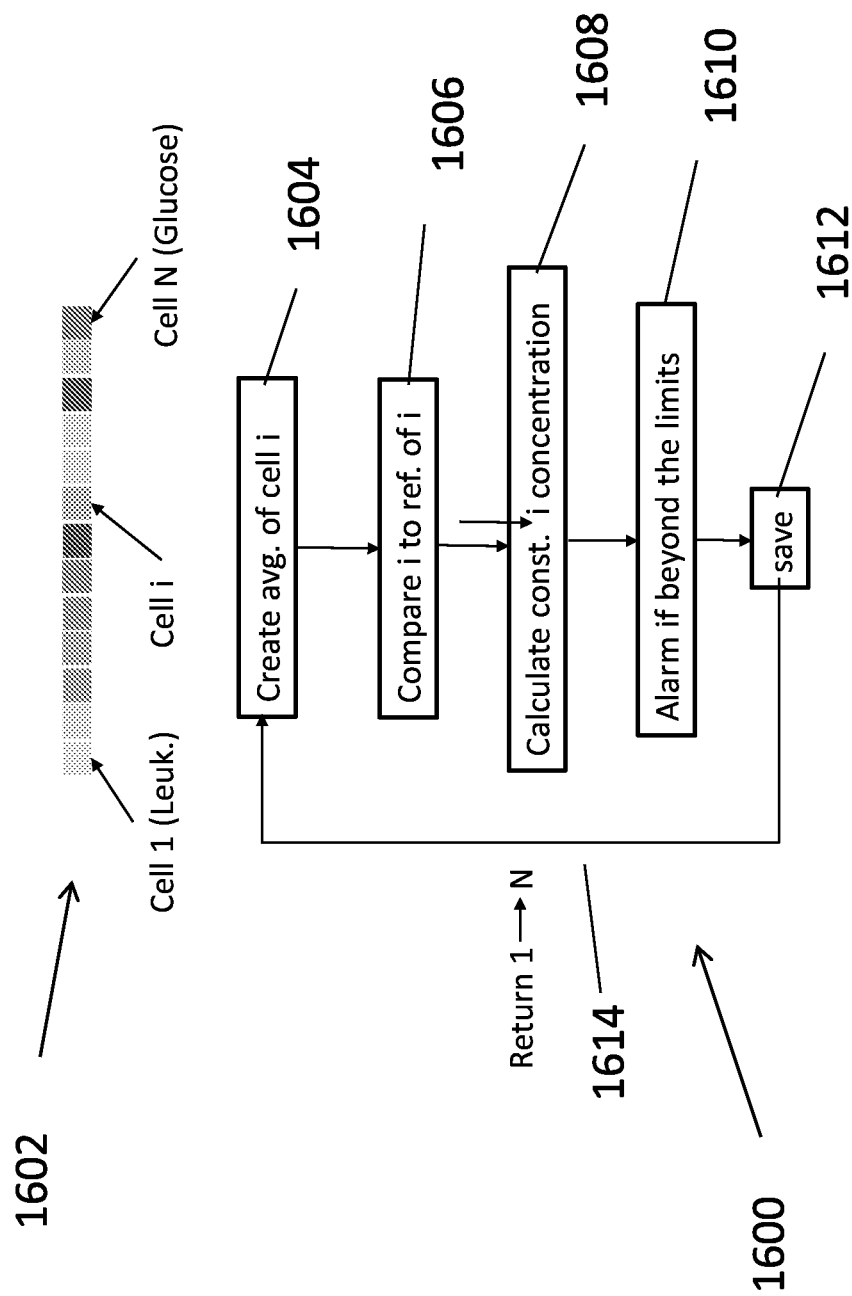
FIG. 16 is a flowchart of a method for calculating concentration of one or more urinary constituents for generating the alert, in accordance with some embodiments of the present invention.

Reference is now made to FIG. 16, which is a flowchart 1600 of a method for calculating concentration of one or more urinary constituents for generating the alert, in accordance with some embodiments of the present invention.

Detector 1602 represents a multi element detector (as described herein) that may be used to identify one or more urinary constituents, for example, using the spectral analysis methods described herein that direct light to different regions of the detector. For example, cell 1 of detector 1602 is used to measure the concentration (or presence) of leukocytes (i.e., white blood cells) in the urine, cell i denotes an arbitrary cell to measure a concentration of an arbitrary constituents, and cell N is used to measure concentration (or presence of) glucose in the urine.

At 1604, an average of multiple readings of different urine drops is calculate for cell i (e.g., optionally for each cell of detector 1602).

At 1606, the average calculated value is compared to a predefined reference value (e.g., empirically measured and/or mathematically calculated based on a model).

At 1608, the concentration is calculated for each urinary constituent according to the comparison of block 1606.

At 1610, the alert is generated according to the concentration in view of the set-of-rules.

At 1612, the alert and/or concentration value may be saved, and/or presented on a display within the GUI.

At 1614, blocks 1604-1612 are iterated to monitor the urine drops of the patient.

Referring now back to FIG. 2, at 218, one or more blocks 202-216 are iterated using new urine drops outputted by the patient.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sensors will be developed and the scope of the term sensor is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A urine analysis device for bed side monitoring of a patient, comprising:
   an inlet sized and shaped for fluid communication with a urine collecting tube that receives urine from a patient;
   a drip chamber through which the urine flows towards an outlet;
   at least one illuminating source for illuminating each respective individual drop of a plurality of drops of urine during fall of the respective individual drop through said drip chamber, said illuminating source is adapted to project light in a perpendicular direction to a falling direction of the respective individual drop;

a sensor that captures only a single image of said each respective individual drop of the plurality of drops during fall of the respective individual drop through said drip chamber upon being triggered by a triggering signal indicating a detection of each respective individual drop of the plurality of drops during fall of the respective individual drop through said drip chamber, wherein said sensor comprises a camera positioned on an opposite side of said drop chamber from said illuminating source;

a photo detector disposed above said sensor, said photo detector generates said triggering signal upon said detection of each respective individual drop of the plurality of drops during fall of the respective individual drop through said drip chamber;

a program store storing code; and a hardware processor coupled to the program store for implementing the stored code, the code comprising:

code to estimate a volume of said each respective individual drop of the plurality of drops during fall of the respective individual drop through said drip chamber by analyzing said only single image to calculate a plurality of cross sectional areas for a plurality of different parts of the respective individual drop;

code to continuously calculate a urine output flow rate of the urine output flowing through the chamber according to the estimated volume of each respective individual drop of the plurality of drops and sum a total volume of the plurality of drops per time interval;

code to continuously calculate and update in real-time, at bedside, a trend in said urine output flow rate by conducting a regression analysis on a plurality of calculated urine output flow rates of said patient;

code to predict a future urine output flow rate based on said continuously calculated trend;

code to output the urine output flow rate, said calculated trend and said predicted future output flow rate to be dynamically displayed in real-time; and code to calculate instructions to control a feeding rate according to the urine output flow.

2. The urine analysis device of claim 1, further comprising code to identify when said trend in the urine output flow rate is indicative of a decrease or increase in the urine output flow rate and to present an indication of the trend on a graphical user interface (GUI) presented on a display.

3. The urine analysis device of claim 1, further comprising code to identify when said trend in the urine output flow rate is indicative of potential acute kidney injury (AKI) and to present an indication of the detected AKI on a graphical user interface (GUI).

4. The urine analysis device of claim 1, further comprising code to generate an alert when said predicted future urine output flow rate is predictive of a future urine flow rate value falling outside of a predefined tolerance range.

5. The urine analysis device of claim 1, wherein the code includes instructions to calculate an instantaneous urine output flow rate, and present the instantaneous urine output flow rate on a graphical user interface (GUI).

6. The urine analysis device of claim 1, further comprising an interface to a display, and code including instructions for presentation of a graphical user interface (GUI) on the display that includes the measured urine output flow rate and an identified trend in the urine output flow rate.

7. The urine analysis device of claim 1, wherein the sensor analyzes urine flowing within the drip chamber, prior to the flowing urine entering a urine collection bag in fluid communication with the outlet.

8. The urine analysis device of claim 1, wherein the camera is a fast gated camera and is activated by said triggering signal generated by said photo detector.

9. The urine analysis device of claim 1, further comprising code to calculate a liquid content type of the respective individual the drop of the plurality of drops of urine by comparing said only a single image of the respective individual drop to an image of each of a plurality of exemplary drops, wherein each of said image of the respective individual drop and said image of each of said plurality of exemplary drops is formed by combining a plurality of time sequentially ordered calculated values of widths of the respective individual drop or one of the plurality of exemplary drops;

wherein each of the plurality of exemplary drops is made of a different one of a plurality of liquid content types; and wherein the respective individual drop of the plurality of drops of urine is calculated to be of one of said plurality of the liquid content types according to said comparison.

10. The urine analysis device of claim 1, wherein the drip chamber is transparent, and wherein the sensor comprises an optical sensor for estimating the volume of each respective individual drop of the plurality of drops through the walls of the transparent drip chamber.

11. The urine analysis device of claim 10, wherein the drip chamber is detachable.

12. The urine analysis device of claim 1, further comprising a drip formation element for forming said urine received through said inlet into single sequentially falling drops.

13. The urine analysis device of claim 12, wherein said drip formation element is designed to form said single sequentially falling drops in a rate that matches a urine flow rate of said received urine from said patient.

14. The urine analysis device of claim 1, wherein said regression analysis is conducted using a least square regression analysis and a sliding time window of a predefined number of calculated urine output flow rates.

15. The urine analysis device of claim 1, wherein said sensor estimates said respective volume of each respective individual drop of the plurality of drops by converting said single image of the respective individual drop to a binary image by processing said at least one image using a binary filter.

16. The urine analysis device of claim 1, wherein said estimating the volume of each respective individual drop of the plurality of drops of urine is by summing a plurality of volumes, each volume of a plurality of volumes being one of a plurality of horizontal planar segments of the respective individual drop, wherein each of said plurality of volumes is calculated by measuring an electromagnetic radiation (EMR) captured within said single image, in a restricted horizontal planar area during a sequence of time intervals, wherein when the respective individual drop falls, in each time interval a different horizontal segment of the respective individual drop interferes with a portion of said EMR reaching the restricted horizontal planar area.

17. The urine analysis device of claim 1, wherein the instructions to control the feeding rate of the feeding device according to the estimated urine output flow comprises instructions to increase or decrease the feeding rate.

18. The urine analysis device of claim 1, further comprising code to calculate instructions to control the feeding device according to the estimated urine output flow to treat the patient for preventing deterioration and/or disease progression.

19. The urine analysis device of claim 1, wherein the instructions to control the feeding rate of the feeding device according to the estimated urine output flow comprises instructions to control the feeding rate of at least one member selected from the group consisting of: diuretic, and fluids.

20. The urine analysis device of claim 1, further comprising code to:
- detect each respective individual drop of the plurality of drops of urine during free fall in said drip chamber;
- generate a time stamp for each detected respective individual drop;
- trigger the sensor for capturing only the single image of each respective individual drop during free fall by the detection of the respective individual drop;
- and compute the urine output flow rate and/or trend of said urine output flow rate based on multiple time sequentially ordered calculated values of widths of each respective individual drop.

* * * * *